US009951369B2

(12) United States Patent
Colin et al.

(10) Patent No.: US 9,951,369 B2
(45) Date of Patent: Apr. 24, 2018

(54) DEVICE DESIGNED TO RECEIVE A BIOLOGICAL SAMPLE

(71) Applicant: BIOMÉRIEUX, Marcy-l'Etoile (FR)

(72) Inventors: Bruno Colin, Marcy l'Etoile (FR); Marie-Pierre Montet, Grezieu la Varenne (FR); Christine Rozand, St. Genis les Olliers (FR)

(73) Assignee: BIOMERIEUX, Marcy-l'Etoile (FR)

( * ) Notice: Subject to any disclaimer, the term of this patent is extended or adjusted under 35 U.S.C. 154(b) by 175 days.

(21) Appl. No.: 14/655,177

(22) PCT Filed: Dec. 27, 2013

(86) PCT No.: PCT/FR2013/053277
§ 371 (c)(1),
(2) Date: Jun. 24, 2015

(87) PCT Pub. No.: WO2014/102517
PCT Pub. Date: Jul. 3, 2014

(65) Prior Publication Data
US 2015/0329893 A1    Nov. 19, 2015

(30) Foreign Application Priority Data
Dec. 28, 2012   (FR) ..................... 12 62966

(51) Int. Cl.
*C12Q 1/04* (2006.01)
*C12M 1/26* (2006.01)
(Continued)

(52) U.S. Cl.
CPC ................ *C12Q 1/04* (2013.01); *B01L 3/502* (2013.01); *B01L 3/505* (2013.01); *G01N 21/78* (2013.01);
(Continued)

(58) Field of Classification Search
CPC ......... B01L 2200/141; B01L 2300/047; B01L 2300/049; B01L 2300/0618;
(Continued)

(56) References Cited

U.S. PATENT DOCUMENTS 5,335,673 A    8/1994   Goldstein

FOREIGN PATENT DOCUMENTS

CN    201795941 U    4/2011
EP    0378353 A2    7/1990
(Continued)

OTHER PUBLICATIONS

International Search Report PCT/FR2013/053277 dated Mar. 6, 2014.

*Primary Examiner* — Michael L Hobbs
(74) *Attorney, Agent, or Firm* — Husch Blackwell LLP

(57) ABSTRACT

A device designed to receive a biological sample and methods of using the same are disclosed. The device includes a leak-proof container, a sampler, and a receptacle. The container includes an enclosure, a filler and a closing mechanism that hermetically closes the filler. The sampler is positioned inside the enclosure. The sampler samples biological and/or physiochemical information from a sample and analyzes the information. The receptacle includes a disinfecting agent that is released when the receptacle is opened. An analysis restrictor inhibits analysis by the sampler. A portion of the sampler and/or the analysis restrictor is designed to shift from a first position that prevents analysis of the sampler to a second position that allows analysis of the sampler. A receptacle opening is mechanically induced when shifting from the first position to the second position.

27 Claims, 8 Drawing Sheets

(51) Int. Cl.
    *G01N 31/22*    (2006.01)
    *G01N 21/78*    (2006.01)
    *B01L 3/00*     (2006.01)

(52) U.S. Cl.
    CPC ............ *G01N 31/226* (2013.01); *B01L 3/523* (2013.01); *B01L 2200/141* (2013.01); *B01L 2300/047* (2013.01); *B01L 2300/049* (2013.01); *B01L 2300/069* (2013.01); *B01L 2300/0618* (2013.01); *B01L 2300/0819* (2013.01); *B01L 2400/0683* (2013.01)

(58) Field of Classification Search
    CPC ....... B01L 2300/069; B01L 2300/0819; B01L 2400/0683; B01L 3/502; B01L 3/505; B01L 3/523; C12Q 1/04; G01N 21/78; G01N 31/226
    See application file for complete search history.

(56) References Cited

FOREIGN PATENT DOCUMENTS

| | | |
|---|---|---|
| FR | 2612297 A1 | 9/1988 |
| WO | WO 2012/004540 A1 | 1/2012 |
| WO | WO 2014/102517 A1 | 7/2014 |

DEVICE DESIGNED TO RECEIVE A BIOLOGICAL SAMPLE

CLAIM OF PRIORITY

The present application is a National Stage filing under 35 U.S.C. § 371 of International Patent Application No. PCT/FR2013/053277, filed on Dec. 27, 2013 and entitled "DEVICE DESIGNED TO RECEIVE A BIOLOGICAL SAMPLE," which claims the benefit of and priority to French Patent Application No. 1262966, filed on Dec. 28, 2012, both of which are incorporated by reference herein in their entireties.

TECHNICAL FIELD

The present invention relates generally to the analysis and/or transfer of biological samples for purposes of analysis. Generally, the present invention aims at reducing the risks of contamination of the environment and/or of personnel within the context of analyses—and more generally of handling—of biological samples, preferably those likely/suspected to contain microbiological material.

STATE OF THE ART

In the field of analysis, particularly that of biological analysis (and more particularly of microbiological analysis), the problem is regularly posed of the safety of technicians who handle biological samples, particularly due to the risks of contamination that exist when an aliquot is taken for purposes of analysis. This is particularly true when analysis devices are used, for example to detect one or more target microorganisms, outside the laboratory within the context of "point-of-care" technologies.

Thus are known the risks taken by technicians required to a sample aliquot from a blood bag intended for transfusion, in order to verify the harmlessness of the sample. Blood bags, due to their flexible walls, are containers far from being easy to handle. It follows that people who handle these blood bags may very easily come into contact with the sample and risk being contaminated if the bags are not pathogen-free.

Contamination may also occur in the opposite direction. For instance, it happens that, during the sampling of biological liquids, such as urine, suspected of being contaminated, the personnel who take the samples contaminate the samples themselves, making it impossible to provide a reliable diagnosis from said samples.

In the case of food samples taken for quality control purposes, it is also very important to ensure that no parasitic contamination is caused by the technician responsible for the analysis.

Moreover, it is common to proceed with cultivation of the food sample taken. This cultivation consists generally in placing the sample in a plastic bag containing culture medium allowing microorganisms, particularly bacteria, to develop. After an incubation period needed for microbiological development, one or more sample aliquots of the culture medium are taken in order to perform a microbiological analysis. The sample aliquot is taken generally at the conclusion of the pre-enrichment/enrichment phase by opening the bag by means of the opening used to add the food sample and the culture medium. Such a process is often critical to carry out insofar as the technician responsible for this procedure must simultaneously keep the bag open, hold the bag closure device and hold the pipette used to withdraw the culture medium. Furthermore, such handling conditions substantially increase analysis time. Thus, productivity may be severely impeded when the number of samples is large.

In view of these problems, the Applicant developed a novel and easy-to-automate process for detecting and identifying microorganisms (and for confirming this detection and/or identification) that particularly limits the handling of the biological sample contained in a container, thus limiting the risks of contamination either of the personnel handling the sample or of the sample itself. This novel process is disclosed in international application WO 2012/004540. According to a preferred embodiment, the detection of the target microorganism(s) is carried out by optical reading of a capture substrate sensitised with at least one binding partner specific to the target microorganism(s) for purposes of optical detection. This optical reading of the result, which is carried out through the transparent wall of the container (a plastic bag or pouch, for example), can be performed visually or by means of an optical reading device.

The process according to WO 2012/004540 allows direct access to the analysis results without requiring handling by the technician. The result is that this process and the devices employed to implement this process can be used outside the laboratory, in the field, to detect, for example, microbial contamination of a biological sample, particularly within the context of medical or food analyses. Consequently, it is important to limit the risks of microbial contamination for users and/or their environment related, for example, to accidental opening of the container (which may result from a rupture or tear in a wall of said container) or to untimely opening of the container due to mishandling.

Moreover, during use outside the laboratory (point-of-care technology) it is important to be able to ensure optimal sterilisation of the container and its contents (including the capture substrate able to contain the target microorganisms) in the absence of autoclave-type sterilisation devices (commonly employed in laboratories).

Furthermore, at the conclusion of the process disclosed in international application WO 2012/004540, the Applicant discovered that it can prove extremely advantageous to retrieve said capture substrate able to contain the target microorganisms (and, optionally, a portion of the biological sample) for subsequent analyses, for example for purposes of confirmation. The transfer of said capture substrate (and, optionally, a portion of the biological sample) must be able to be carried out without risk of contamination for the user and/or the environment.

The invention thus aims at solving all or part of the above-referenced problems.

SUMMARY OF THE INVENTION

Consequently, an object of the invention concerns a device designed to receive at least one biological sample, said device comprising:
  at least one container, preferably leak-proof, designed to receive said biological sample, said container comprising at least one filling means, such as an orifice (or an opening), and at least one closing means designed to close said filling means, preferably hermetically,
  at least one sampling means positioned inside the enclosure of said container, stationary or movable, said sampling means being designed to sample biological and/or physicochemical information from said biological sample, said sampling means being designed to be analysed after said biological and/or physicochemical information is sampled and/or placed in a release position, and at least one receptacle, such as a pouch or a compartment, comprising at least one disinfecting agent, said disinfecting agent being designed to be released inside the container after said receptacle is opened, when said sampling means is designed to be analysed after said biological and/or physicochemical information is sampled, at least one analysis restricting means separate from said sampling means, stationary or movable, partially or completely restricting, preferably completely, the analysis of said sampling means, wherein at least a portion of said sampling means and/or at least a portion of the analysis restricting means are/is designed to shift from a first position, wherein the analysis of said sampling means and/or the release of said sampling means from said container are/is difficult or impossible, preferably impossible, to a second position, wherein the analysis of said sampling means and/or the release of said sampling means from said container are/is possible, and wherein said portion of said sampling means and/or said portion of the analysis restricting means are/is connected to said receptacle such that the opening of said receptacle can be caused/activated mechanically by shifting from said first position to said second position.

Thus, said portion of said sampling means and/or said portion of the analysis restricting means are/is connected to said receptacle by a connection/link of such nature that shifting from said first position to said second position causes/activates the opening of said receptacle. Said connection/link may be a wire, for example.

Preferably, said receptacle comprises an opening means, such as a rupture means, said disinfecting agent being designed to be released inside the container after opening said opening means. By "opening means" is meant any means that allows the opening (by rupturing, breaking, tearing, etc.) of said receptacle during the shifting from the first position to the second position. In other words, said portion of said sampling means and/or said portion of the analysis restricting means are/is connected to said opening means such that the opening of said opening means can be caused/activated mechanically by shifting from said first position to said second position.

For example, such an opening means may comprise/consist of weakened area present on said receptacle, for example at the junction between the latter and the mechanical connection (such as a wire), the opening of this opening means resulting from the force exerted on said opening means by said connection during the shifting of at least a portion of the sampling means and/or of at least a portion of the analysis restricting means from said first position to said second position.

In short, the device according to the invention is designed to shift from the first conformation/configuration wherein the analysis and/or the release of said sampling means from said container are/is difficult or impossible, preferably impossible, to the second conformation wherein the analysis and/or the release of said sampling means from said container are/is possible.

According to a preferred embodiment, the container contains at least one cultivation means, such as culture medium, preferably in dehydrated form. This/these cultivation means is/are important, even essential, in order to allow/promote— if need be following a rehydration step (in the case of dehydrated cultivation means)—growth of the target microorganisms. This is true particularly when the biological sample of interest is likely/suspected to contain a minimal amount of target microorganisms.

The invention also relates to a device designed to receive at least one biological sample, said device comprising:

at least one container, preferably leak-proof, designed to receive said biological sample, said container comprising at least one filling means, such as an opening, and at least one closing means designed to close said filling means, preferably hermetically, at least one sampling means positioned inside the enclosure of said container, stationary or movable, said sampling means being designed to sample biological and/or physicochemical information from said biological sample, said sampling means being designed to be analysed after said biological and/or physicochemical information is sampled, and at least one receptacle, such as a pouch or a compartment, comprising at least one disinfecting agent, said disinfecting agent being designed to be released inside the container after said receptacle is opened, at least one analysis restricting means separate from said sampling means, stationary or movable, partially or completely restricting, preferably completely, the analysis of said sampling means, wherein at least a portion of said sampling means and/or at least a portion of the analysis restricting means are/is designed to shift from a first position wherein the analysis is difficult or impossible ("analysis restricting position"), preferably impossible, to a second position wherein the analysis of said sampling means is possible ("analysis position"), and wherein said portion of said sampling means and/or said portion of the analysis restricting means are/is connected to said receptacle such that the opening of said receptacle can be mechanically induced by shifting from said first position to said second position.

The invention also relates to a device designed to receive at least one biological sample, said device comprising:

at least one container, preferably leak-proof, designed to receive said biological sample, said container comprising at least one filling means, such as an opening, and at least one closing means designed to close said filling means, preferably hermetically, at least one movable sampling means positioned inside the enclosure of said container, said sampling means being designed to sample biological and/or physicochemical information from said biological sample, said sampling means being designed to be placed in a release position, and at least one receptacle, such as a pouch or a compartment, comprising at least one disinfecting agent, said disinfecting agent being designed to be released inside the container after said receptacle is opened, wherein at least a portion of said sampling means is designed to shift from a first position wherein the release of said sampling means from said container is difficult or impossible, preferably impossible, to a second position wherein the release of said sampling means from said container is possible ("release position"), and wherein said portion of said sampling means is connected to said receptacle such that the opening of said receptacle can be mechanically induced by shifting from said first position to said second position.

The release position of said sampling means is a position at which said sampling means projects at least partially from the surface of said container, a position wherein said sampling means is able to be hermetically separated from said container, for example by heat sealing (heat welding) and cutting. This release position may also be called the transfer position, insofar as it allows the transfer of said sampling means, after release of the latter, to another container, for example for purposes of analysis/analysis confirmation.

By "biological sample" is meant, in the sense of the present invention, a defined amount of a material, substance or product likely/suspected to contain biological material, such as microbiological material.

According to the present invention, the biological sample may come from a variety of sources, for example from food, from the environment, from veterinary activities or from clinical activities. Among samples of food origin, mention may be made, but in a non-limiting manner, of a sample of milk products (yoghurt, cheese, etc.), of meat, of fish, of eggs, of fruit, of vegetables, of water, of beverages (milk, fruit juice, soda, etc.). Obviously, these samples of food origin may also come from sauces or from more elaborate dishes or from unprocessed (or partially processed) raw materials. A food sample may also come from animal feeds, such as oil cakes or animal flours.

As indicated above, the biological sample may be of environmental origin and may consist of, for example, a surface sample, a water sample or an air sample.

The biological sample may also consist of a biological sample of clinical origin, such as a sample of biological fluid (whole blood, serum, plasma, urine, cerebrospinal fluid, etc.) or of stool (choleraic diarrhoea, for example), or samples from the nose, throat, skin, wounds, organs, tissues or isolated cells. This list is obviously not exhaustive.

Generally, the term "sample" refers to a portion or an amount (more particularly a small portion or a small amount) taken from one or more entities for purposes of analysis. Optionally, this sample may have undergone a preliminary treatment involving, for example, steps of mixing, dilution or crushing, particularly if the starting entity is a solid.

The biological sample taken is, in general, likely to—or suspected to—contain at least one target microorganism. In most cases, the latter is a pathogenic microorganism (such as *Salmonella* or *Vibrio cholerae*) that for medical purposes it is advisable to detect. This target microorganism may also consist of an antibiotic-resistant bacterium.

Due to its nature and its applications, the present invention is suited particularly to the analysis and transfer for purposes of analysis of biological samples having potentially moderate to significant (even extremely significant) pathogenicity, such as a sample of choleraic diarrhoea.

As indicated above, the closing means is, preferably, a hermetic closing means aiming at sealing the container of the device according to the invention. This closing means may be reversible or permanent (irreversible). The latter embodiment is particularly advantageous insofar as it makes it possible to avoid reopening (due to user error, for example) the closing means after introducing the biological sample into the container.

As reversible closing means, mention may be made, for example, of a standard cap or a closing means attached reversibly by sticking. In the latter case, shifting from the closed position to the open position of said closing means is carried out by unsticking the latter. Conversely, the closing operation is carried out by sticking said closing means on the corresponding part of the container comprising the opening.

According to a preferred embodiment, the filling means comprises/consists of a hollow appendage (tube-shaped, for example) having an open end intended to receive the biological sample of interest, the other end being connected to said container, preferably on one of the sides of the container, advantageously made of the same material as the latter. Preferably, said open end is flared in shape, for example is funnel-shaped, in order to facilitate the collection of the biological sample.

Advantageously, this appendage is tube-shaped and its diameter decreases from the open end to that connected to said container.

In this preferred embodiment, the closing means comprises/consists of a heat-sealable/heat-weldable area located at the end of the appendage connected to said container. In this case, said appendage is closed, in a permanent manner, by heat sealing, then by cutting, preferably by means of a sharp tool. In order to carry out this heat sealing, a heat-sealing device that heat seals said heat-sealable area and, preferably, in the same operation, cuts the area thus heat sealed is preferably used. Alternatively, and particularly when operational conditions are rudimentary (when the device according to the invention is used in the bush, for example, far from all conveniences provided in so-called "industrialised" countries), this heat-sealing and cutting operation may be carried out by means of a cigarette lighter and a simple pair of scissors.

When a heat-sealing device is used, the latter has, advantageously, a temperature indicator (such as an indicator light) that indicates to the user that the temperature created by the heat-sealing device is adequate.

By "at least one biological and/or physicochemical information sampling means" is meant, in the sense of the present invention, any means allowing the extraction/capture of said biological and/or physicochemical information. Illustratively, said sampling means may consist of:

i) a biological and/or physicochemical information capture means, for example:
  i.1) a selective capture means, such as a capture substrate functionalised/sensitised with a binding partner of a microorganism to be detected, or
  i.2) a non-selective capture means, for example comprising/consisting of an absorption means (a spongy component, such as cotton, or a compressible component, such as sponge, for example), pH paper or an indicator of the formation or presence of a particular substrate (such as $H_2S$ formation) intended to be contacted with said biological sample; or
ii) a simple receptacle (consisting of a folded flexible membrane, for example) that can receive at least a portion of the biological sample.

Obviously, the device according to the invention may comprise several sampling means, for example a combination of said sampling means i) and ii). On a purely illustrative (and non-limiting) basis, said device may comprise:

as first sampling means: a receptacle ii) consisting of a flexible membrane connected to the container, said flexible membrane being designed to be invaginated inside the container in said first position and at least partially evaginated outside the container in said second position, and as second sampling means: a biological and/or physicochemical information capture means i) positioned on the surface of said flexible membrane in a position designed to be in contact with the biological sample in said first position and to be no longer in contact with said biological sample in said second position.

The "biological and/or physicochemical information" feature should be interpreted in the broad sense within the context of the present invention as comprising biological material as such, or at least a component thereof (particularly of genetic nature, such as DNA, RNA or derivatives thereof, or of protein nature, such as proteins or amino acids), as well as information of a biochemical or physicochemical nature (such as pH).

Biological material means any material that contains genetic information and that is self-propagating in a biological system. As such, particular mention may be made of prokaryotic or eukaryotic cells, bacteria or viruses.

The manner in which the various components of the device according to the invention are organised and structured together defines a particular conformation, namely a configuration, a specific spatial (three-dimensional) arrangement.

As indicated above, the receptacle comprising a disinfecting agent may consist particularly of a pouch, for example seated and attached inside the container by a rigid seat. The wall of this pouch or this compartment is designed to prevent any exchange of the contents of the pouch or the compartment (containing at least one disinfecting agent) with the inside of the container in said first position.

The disinfecting agent(s) may be present particularly in powder, liquid or pellet form, etc. The nature of this/these disinfecting agent(s) and the amount in which the latter is used are selected specifically such that all microorganisms pathogenic to humans and animals and growing in the contents (during an incubation phase, for example) are destroyed when the disinfecting agent is released inside the container during the shifting from the first position to the second position.

For example, the disinfecting agent (or agents) is an antimicrobial agent, such as an antibacterial, a virucide, a fungicide.

The disinfecting agent(s) may be released inside the container after said receptacle is opened. This receptacle may be opened by any suitable means. According to a preferred embodiment the receptacle is a pouch having a weaker area (also called rupture means) allowing it to open during any mechanical operation carried out at said weaker area. This mechanical operation may be of the rupture, tearing or crushing type, etc.

The connection between at least a portion of said device separate from said sampling means and at least a portion of the sampling means is a mechanical connection/link (such as a wire) between:
  at least a portion of the device according to the invention separate from said sampling means and/or at least a portion of said sampling means, and
  said receptacle.

In other words, at least a portion of the device according to the invention other than said sampling means, or said sampling means, or both, can be shifted from said first position to said second position, this shifting from said first position to said second position generating force by means of the connection/link exerted on said receptacle, said force resulting in the opening of the latter. According to the preferred embodiment wherein the receptacle is a pouch having a weaker area allowing it to open during any mechanical operation carried out at this weaker area, the connection between at least a portion of said device other than said sampling means and/or at least a portion of said sampling means and said receptacle is made at the weaker area of the receptacle, such that mechanically shifting at least a portion of the device other than the sampling means and/or the sampling means from the first position to the second position causes the opening of this pouch, for example by rupturing, tearing or crushing.

Said receptacle may be placed inside or outside the container, preferably inside the latter, on condition that the disinfecting agent(s) can be released inside the container in said second position. The receptacle may, for example, consist of a preformed compartment within said container or a separate compartment, assembled inside the container, for example via a weld at the base of said compartment.

The container according to the invention may be any container (closed container) designed to receive, analyse and/or transfer a biological sample. This container may be of various types (bag, tube, pouch, etc.). According to a preferred embodiment, the container is made at least partially of flexible material. Preferably, this flexible material is sufficiently rigid that the container maintains a satisfactory position inside the device according to the invention, such that the latter may be stored (during the incubation period, for example, if incubation is employed) without requiring the use of a holder. The absence of the need to use such a holder is particularly advantageous within the context of the use of said device outside the laboratory.

According to a particularly preferred embodiment, said container is made at least partially, preferably entirely, of a polyester-type polymer, such as polyethylene terephthalate (PET), polybutylene terephthalate, polyethylene naphthalate (PEN), the saturated polyester preferably being polyethylene terephthalate (PET).

Preferably, said container consists at least in part—and preferably entirely—of at least one layer of paper or bio-based product sufficiently thick to maintain a satisfactory position in the device according to the invention, or of at least one layer of paperboard, said paper, bio-based product or paperboard preferably being coated on each of its inside and outside surfaces with at least one layer of saturated polyester, preferably PET. Illustratively, the saturated polyester, preferably PET, is present in a concentration of 3% to 10% by weight, the remaining 90% to 97% being composed of said paper or said paperboard. In this embodiment, the container may, if need be, be at least partially deformed in order to limit the bulk of the device according to the invention, subject to maintaining the integrity of the container's wall(s). This deformation may, for example, consist in folding like an accordion.

According to a preferred embodiment, said paper or said paperboard is coated on its inside surface with a colouring agent that is invisible when said colouring agent is not wet (is not in contact with a liquid component) but that, after contact with a liquid component, causes colouring of said paperboard or said paper. This makes it possible to easily detect a defect, such as an abrasion or a hole, on the inside and/or outside surface of said paperboard or paper consisting of at least one layer of polyester-type polymer, said defect being able to allow contamination of the environment (of which the user is a part) and/or of the biological sample.

The analysis of the biological and/or physicochemical information sampling means may be carried out by means of at least one analysis means for directly or indirectly measuring one or more biological and/or physicochemical parameters of a biological sample (pH variation, for example) in order to demonstrate the presence of a contaminant or a particular marker in said sample. Preferably, such an analysis means allows the direct or indirect analysis of the target microorganism(s), as well as all or part of the properties thereof and any change in the medium generated by said microorganism(s) such as pH colour change, for example.

This biological and/or physicochemical information sampling means, when designed to be analysed after contacting said biological sample, may comprise an indicator, marker or other tracer that can be analysed/detected by means of the aforementioned analysis means.

The biological and/or physicochemical information sampling means may also comprise a concentration means, such as an immunoconcentration means, in order to obtain a sufficient concentration on said sampling means of the microorganism(s) of interest, particularly in order to allow the transfer of the target microorganism(s) to another container for purposes of analysis and/or confirmation by hermetically separating said sampling means in its release position.

The analysis of said sampling means may, in a non-limiting manner, be visual or optical analysis, preferably visual, electrical analysis (particularly by measuring electrical impedance), wave analysis (Raman, intrinsic fluorescence, etc.) or mass spectrometry analysis, and may generally be carried out by any analysis means making it possible to analyse said biological and/or physicochemical information for purposes of, for example, directly or indirectly verifying the presence on the sampling means of the microorganism(s) tested.

Visual analysis, as mentioned above, may be carried out directly by observing the sampling means (in order to detect the appearance of staining on the latter, for example) or via an optical amplification means (for increasing resolution and/or detection sensitivity, for example) interfaced between the sampling means and the human eye in order to allow or, at the very least, to facilitate reading of the result by the operator. According to a preferred embodiment, this optical amplification means is included in a telecommunications means, such as a smartphone. Thus, the result may be read:
  directly by the on-site operator by visual reading of the sampling means, and/or
  by an off-site analyst (namely located at a distance from the sampling site, for example several hundred or thousands of kilometers therefrom).

According to a particular embodiment, the result is read by the on-site operator and the off-site analyst, the latter confirming or invalidating the initial analysis performed by the operator.

According to a preferred embodiment, said portion of the analysis restricting means is designed to cooperate with said portion of the sampling means in said first position in order to render the analysis of said sampling means within the container difficult or impossible, preferably impossible, in said first position, said portion of the analysis restricting means being designed to be released partially or completely, preferably completely, from said portion of the sampling means and/or conversely in said second position in order to allow the analysis of said at least one sampling means without removing the latter from said device.

In other words, at least a portion of said sampling means and/or said analysis restricting means are/is connected to said receptacle, shifting from said first position to said second position consisting in partial or complete release, preferably complete, of said analysis means from said analysis restricting means and/or the reverse.

The analysis restricting means is selected according to the type of analysis used and the nature of the biological and/or physicochemical information sampling means to be analysed. As this analysis restricting means, any means may be used on condition that it restricts at least partially—and preferably completely—the analysis of said analysis means in said first position. Illustratively, when the analysis is of the electromagnetic type, the analysis restricting means may be composed of a Faraday cage positioned such that the electromagnetic analysis of the sampling means in said first position is partially or completely (preferably completely) restricted. This analysis is not possible after the Faraday cage is withdrawn, since the withdrawal thereof mechanically causes the receptacle comprising at least one disinfecting agent to open. For example, a metal sheath (tube-shaped, for example) may be used as a Faraday cage.

By partial or complete release, preferably complete, of said analysis restricting means from said sampling means and/or the reverse is meant, in the sense of the present invention:
  withdrawal of the analysis restricting means, expressed as shifting said analysis restricting means from said first position to said second position; and/or
  shifting said biological and/or physicochemical information sampling means from said first position to said second position;
  this shifting being sufficient to allow the analysis of said sampling means in said second position.

In other words, in order to be able to analyse said sampling means, said analysis restricting means is withdrawn, for example by exerting force, such as pulling or rotational force, on the latter, or said sampling means is shifted, for example by exerting force, such as pulling or rotational force, on the latter, or both.

Thus, the operator, desiring to carry out the analysis of said sampling means by any suitable analysis technique and means, is compelled to exert force in order to release said analysis restricting means from said sampling means and/or the reverse, said force being passed along according to a particular embodiment by the mechanical connection/link between at least a portion of the sampling means and/or of the analysis restricting means and the receptacle, thus causing the latter to open, for example by rupturing or tearing, preferably on the weakened area of the receptacle.

Advantageously, said sampling means is designed to be analysed in said second position, said sampling means comprising at least one biological and/or physicochemical information capture means designed to be contacted with said biological sample in said first position and analysed in said second position.

This biological and/or physicochemical information capture means may consist of:
  a selective capture means, such as a capture substrate functionalised/sensitised with a binding partner of a microorganism to be detected, or
  a non-selective capture means, for example comprising/consisting of an absorption means (a spongy component, such as cotton, or a compressible component, such as sponge, for example) or pH paper intended to be contacted with said biological sample.

According to a particularly preferred embodiment, said capture means is designed to be analysed, in said second position, by visual or optical reading, preferably by visual reading, said analysis restricting means being a component restricting at least partially, preferably completely, the transmission of light information between said sampling means and the human eye or said optical reading means in said first position.

Optical reading may be carried out via at least one optical reading means, such as a camera or a Raman spectroscope or any system allowing said optical reading, positioned outside the container, particularly in order to directly or indirectly detect the presence on the sampling means of the microorganism(s) of interest.

According to this preferred embodiment, said biological and/or physicochemical information sampling means comprises a means designed to emit a light signal in the visible, infrared or ultraviolet spectrum, preferably in the visible spectrum (colour or fluorescence, for example) such that this light signal may be detected by visual or optical reading, preferably by visual reading.

As indicated above, for purposes of optical detection, an optical reading means positioned outside the container, such as a camera or a Raman spectroscope, is used. Advantageously, an optical reading means designed to be used in the field, namely outside the laboratory, such as a portable Raman spectroscope, is used.

Depending on the position of the reading area, visual or optical reading may be carried out:
- when said capture means is no longer in contact with the biological sample (and, optionally, the culture medium), or, conversely,
- when said capture means is still in contact with said biological sample (and, optionally, the culture medium).

According to a preferred embodiment, the component restricting at least partially, preferably completely, the transmission of light information between said sampling means (said capture means, in the case in point) and the human eye or said optical reading means in said first position consists of at least one opaque area on at least one wall of said container and/or consists of a movable mask, preferably positioned inside said container.

Thus, the device according to the invention comprises at least one container (a bag, for example), which may have on at least one of its walls an opaque area partially or completely restricting, preferably completely, visual or optical reading of said sampling means in said first position. In this first configuration, the operator cannot carry out visual or optical reading of the biological and/or physicochemical information sampling means. This operator, desiring to carry out visual or optical reading of said sampling means, is compelled to exert force, for example of the pulling or rotational type, on said sampling means in order to convey the latter to the area of the device having at least one translucent or transparent wall ("reading area"), preferably transparent, in order to be able to carry out visual or optical reading of said sampling means and thus to obtain the result of interest. According to a preferred embodiment, the force exerted on said sampling means in order to shift the latter to said reading area is mechanically passed along to the receptacle via the link between the latter and the sampling means in order to open said receptacle and to release said at least one disinfecting agent inside the receptacle.

According to a particularly preferred embodiment, all the walls of the container are opaque, thus preventing the visual or optical analysis sampling means (said biological and/or physicochemical information capture means, in the case in point). The reading area is thus found outside said container but still within the enclosure of the device according to the present invention, for example in an area outside said container but connected to the latter via a flexible membrane (in this case the reading area is located between the flexible membrane and the wall of said container to which said flexible membrane is connected).

Concerning the use of a movable mask, such as a removable opaque sheath at least partially enveloping said sampling means, force, for example of the traction or rotational type, is exerted on said movable mask in order to withdraw it completely or partially, preferably completely, from the biological and/or physicochemical information sampling means in order to render said sampling means available for visual or optical reading, preferably optical. In this embodiment, the sampling means is preferably stationary and the movable mask is designed to shift from a first position restricting visual or optical reading to a second position allowing visual or optical reading. According to a particular embodiment, both the sampling means and the mask may also be movable from a first position to a second position.

Advantageously, said biological and/or physicochemical information capture means consists of a microorganism(s) capture means, such as a capture substrate designed to capture the microorganism(s) of interest, said microorganism(s) capture means being designed to be analysed, after capture of the microorganism(s) of interest, by at least one analysis means.

The connection/link (such as a wire) between the receptacle and said sampling means and/or said analysis restricting means is configured in such a way that the disinfection caused by shifting from said first position to said second position occurs:
- when said capture means is no longer in contact with the biological sample (and, optionally, the culture medium), or, conversely,
- when said capture means is still in contact with said biological sample (and, optionally, the culture medium).

Although these two options are comprised within the scope of the present invention, the first scenario is particularly advantageous insofar as it makes it possible to preserve the integrity of the microorganism(s) of interest, which may prove to be important in terms of cultivating or re-cultivating the latter for purposes of analysis confirmation.

It should be noted that, even in the second scenario, an analysis confirmation may be performed on dead microorganisms, particularly by means of molecular biology/genetic identification techniques (such as PCR).

An example of a microorganism(s) capture means that may be used according to the present invention is a capture substrate functionalised/sensitised with a specific or non-specific (preferably specific) binding partner of the at least one target microorganism. According to a preferred embodiment, the specific binding partner is selected from the group consisting of antibodies, Fab fragments, Fab' fragments, recombinant or non-recombinant phage proteins, phages, aptamers or any other relatively specific ligand well-known to the skilled person.

The presence on the capture substrate of target microorganisms may be revealed by means of any suitable detection system, that is, one able to detect the target microorganism(s). By "detection system" is meant any molecule that is able to couple with the microorganisms or the binding partners of said microorganisms and that makes it possible, by its transduction properties (fluorescence, staining, radioactivity, etc.) to detect the presence of said microorganisms. This detection of the presence of target microorganisms may be obtained particularly by visualisation or optical reading, as indicated above, of staining (such as red staining due to 2,3,5-triphenyl tetrazolium chloride (TTC) reduction by the microorganisms of interest) or of fluorescence on all or part of the capture substrate.

According to a preferred embodiment, the detection system is based on the reduction by microorganisms of certain tetrazolium salts, particularly 2,3,5-triphenyl tetrazolium chloride by said microorganisms. As they grow, said microorganisms take in TTC (colourless in its non-reduced form) and then reduce it to triphenyl-formazan (red in colour), thus staining in red the microorganisms present on the capture substrate. This staining can then be detected by visual or optical reading in said second position.

As capture substrate, particular mention may be made of particulate substrates, optionally magnetic, or single-piece substrates, optionally porous. The capture substrate may be simply an inert substrate, such as a sheet of plastic material or glass fibre, or, advantageously, may be sensitised with an optionally specific binding partner. The capture substrate may also consist of a compressible single-piece substrate. According to a particular embodiment, the capture substrate may be of one with the detection means. This is the case, for example, when the capture substrate is composed of an electrochemical biosensor or an optical fibre.

Concerning the binding partner, when such a binding partner is attached to a capture substrate, it is advantageously selected from antibodies, Fab fragments, Fab' fragments, recombinant or non-recombinant phage proteins, phages, lectins, aptamer-type nucleic acids or any other ligand well known to the skilled person.

According to a particularly preferred embodiment, the sampling means is designed to be placed in a release/separation position, said means consisting of a flexible membrane connected to said container, said flexible membrane being designed to be invaginated inside the container in said first position and at least partially evaginated outside the container in said second position ("release position").

This flexible membrane consists, in the sense of the present invention, of a flexible and hermetic membrane/wall, in order to avoid risks of contamination.

The first position (invaginated) is a position wherein said flexible membrane penetrates by turning inside-out into a glove finger (inside-out glove finger shape) inside said container.

Shifting from the invaginated position to the evaginated position is carried out by turning inside-out like a finger of a glove said flexible membrane, which, in the evaginated position, projects from the surface of said container in the shape of a finger of a glove.

This inside-out glove finger shape, invaginated inside the container, protects the integrity of said flexible membrane in said first position (which may be called the "protection position"), which is the position wherein the device according to the invention is stored and/or transported. This inside-out glove finger shape of the sampling means thus makes it possible to limit the risks of tearing, rupturing or other breaches in the flexible membrane constituting the sampling means during storage and transport of the device according to the invention.

According to this embodiment, said sampling means may be "passive", namely it does not comprise a biological and/or physicochemical information capture means but allows the sampling for purposes of transfer for subsequent analysis/analyses of an aliquot of the biological sample of interest. Obviously, in its invaginated position ("first position" or "protection position"), the sampling means does not allow such sampling. Sampling is possible in the second position ("release position" or "transfer position"), namely when said sampling means is at least partially evaginated (namely it projects at least partially from the surface of said container).

Shifting said sampling means from the first position (invaginated) to the release position (at least partially evaginated) may be carried out, for example, by applying pulling force on a gripping means connected to the outside surface of said flexible membrane or, preferably, by generating excess air pressure (by compressing at least one flexible wall of said container, for example) inside said container, in order to cause the "evagination" of said sampling means, namely the turning inside-out into a glove finger shape of said flexible membrane. Obviously, and particularly in the embodiment according to which said at least one flexible wall is designed to be compressed in order to cause the evagination of the sampling means by means of excess air pressure, the wall(s) and flexible membranes, and, more generally, the various components of the device according to the invention, are carefully selected such that their integrity is preserved during the shifting from the invaginated position to the evaginated position. This is important in order to guarantee the health and safety of the operator and his/her environment.

In the second position ("release position"), the aliquot of the biological sample of interest may be introduced into the glove finger formed by the evaginated sampling means by any means, for example simply by sufficiently tilting the device according to the invention such that a portion of the biological sample flows into the evaginated sample means. An alternative for introducing the desired aliquot into the sampling means in said release position consists, for example, in compressing the container with sufficiently great intensity such that a portion of the biological sample (and, optionally, of the culture medium) is transferred from said container to the sampling means in the release position (shaped like the finger of a glove, as indicated above). In the latter case, it is necessary that at least one wall of said container is deformable (made at least partially of supple or flexible material, for example), such that the compression applied to this/these deformable wall(s) can deform the latter and thus cause the transfer of at least a portion of the biological sample (and, optionally, of the culture medium) via an increase in the level in the latter within said container without danger to the operator and the environment.

For purposes of clarity, it should be noted that, in this embodiment, at least a portion of said sampling means is connected to said receptacle by a mechanical connection/link designed to cause the opening of said receptacle when said sampling means shifts from its first position (invaginated position) to its release position (evaginated position).

Consequently, the simple fact of carrying out this procedure of transferring the biological sample from the container to said sampling means in the evaginated position (second position) will, ipso facto, cause the disinfection of the portion of the biological sample remaining within said container after said transfer procedure. Thus, and without specific action by the operator aiming to cause the disinfection of the container, disinfection of the biological material remaining within said container is automatically/systematically obtained.

According to an advantageous embodiment, said flexible membrane comprises at least one biological and/or physicochemical information capture means, said biological and/or physicochemical information capture means being positioned on the surface of said flexible membrane in a position designed to be in contact with the biological sample in said first position and to be no longer in contact with said biological sample in said second position.

The positioning of said biological and/or physicochemical information capture means on the surface of said flexible membrane is defined such that this capture means is in contact with the biological sample when said sampling means is in the invaginated position in the container, namely has the shape of an inside-out finger of a glove, and such that it is no longer in contact with said biological sample in the at least partially evaginated position outside the container, namely in the shape of a finger of a glove. Continuing the glove finger/inside-out glove finger analogy, the biological and/or physicochemical information capture means is preferably positioned at the end of the inside-out glove finger in contact with the biological sample in the first position (invaginated). This embodiment is particularly preferred since it provides the option, in addition to the fact of optionally being able to take an aliquot of the biological sample of interest for purposes of transfer as described above, of carrying out the capture of at least one piece of biological and/or physicochemical information of interest in the first position (invaginated position) by leaving said capture means in contact with the biological sample of interest for an amount of time sufficient to carry out the capture of the biological and/or physicochemical information of interest, then, secondly (when the operator estimates that the capture means has remained in contact with the biological sample for a sufficient amount of time), of carrying out the transfer of said capture means by exerting force, for example of the pulling or rotational type, on said sampling means in order to shift it from its first position (invaginated) to its release position (evaginated). Once the release position is reached, the operator may, if desired, hermetically separate (release) the sampling means containing said biological and/or physicochemical information capture means (and, optionally, an aliquot of the biological sample) in order to send said sampling means separated from the container to a laboratory for purposes of, for example, carrying out the analysis and/or analysis confirmation of said capture means "trapped" inside the heat-sealed sampling means. As indicated above, and if it is in accordance with the operator's wishes, in addition to the biological and/or physicochemical information capture means, the sampling means hermetically separated from said container may comprise an aliquot of the biological sample initially introduced into the container. This may prove advantageous particularly if it is sought to (re-)cultivate all or part of the biological material, particularly the biological material found in this aliquot.

According to a particular embodiment, before hermetic separation of the sampling means, the latter may be analysed in said release position. In this configuration, the biological and/or physicochemical information capture means is, preferably, a microorganism(s) capture means as defined above, advantageously designed to be analysed by visual or optical reading in said release position; the flexible membrane constituting the sampling means being, in this embodiment, translucent or transparent, preferably transparent, in order to allow visual or optical reading of the microorganism(s) capture means. Advantageously, the walls of the container are opaque such that this analysis by visual or optical reading cannot be carried out within the container but requires shifting said sampling means, comprising the microorganism(s) capture means, from a first position wherein the analysis of said microorganism(s) capture means is impossible to said second position corresponding, in this embodiment, both to the analysis position and to the release position, and wherein the analysis by visual or optical reading is possible prior to the release of said sampling means. The opaque walls of the container correspond, in this embodiment, to said analysis restricting means. The latter is, still in this embodiment, stationary, whereas the sampling means is designed to shift from a first position wherein visual or optical reading is impossible to a second position wherein it is possible.

Thus, the device according to the present invention provides the operator a very wide range of use. Indeed, the operator may, if desired:

- use said device simply to transfer an aliquot of the biological sample of interest to another container in order to, for example, carry out more thorough analyses;
- transfer at least one biological and/or physicochemical information capture means having been contacted beforehand with the biological sample to be analysed to another container in order to carry out an additional analysis and/or analysis confirmation;
- carry out the analysis, preferably by visual or optical reading, of said biological and/or physicochemical information capture means present on said sampling means, in the release position, optionally prior to such a transfer, etc.

The preferential shape of the sampling means according to the invention in its first position (invaginated position), namely the shape of an inside-out glove finger whose end at least is in contact with the biological sample of interest in said first position, is particularly advantageous when at least one biological and/or physicochemical information capture means is positioned at this end in order to be in contact with the biological sample in the starting position, since the operator may slip his/her finger inside the sampling means shaped like an inside-out finger of a glove in order to shift the biological and/or physicochemical information capture means to one or more areas of interest. This may have an advantage particularly if the biological sample is in semi-solid form (such as a stool sample) or if the sample is not correctly/sufficiently homogenised. Thus, the operator may manually direct the biological and/or physicochemical information capture means to/in the areas of the biological sample or may legitimately wait until the biological and/or physicochemical information of interest is present in a greater amount.

According to a preferred embodiment, the receptacle also comprises at least one marker, such as a coloured marker, for verifying the release said disinfecting agent inside the container after said receptacle is opened.

Such a coloured marker may consist, on a purely illustrative basis, of a coloured indicator whose colour changes under the effect of a variation of pH.

Preferably, the disinfecting agent(s) is/are present in excess within the receptacle in order to ensure sufficient disinfection of the inside of the container even in the event of a partial release.

The appearance of colouring related to said coloured marker in the contents of said container (comprising particularly the biological sample) confirms the opening of said receptacle and/or the effective disinfection of all or part of the inside of the container after the operator performs an analysis and/or biological sample transfer operation. This effective disinfection results from the homogeneous distribution of the disinfectant inside the container and the destruction of microbes therein.

According to a preferred embodiment, said sampling means is connected to said container by a tamper-evident means, such as a tamper-evident ring.

According to a preferred embodiment, the device according to the invention comprises a plurality of identical or different sampling means positioned inside the enclosure of said container, the sampling means being joined together in such a way that shifting from said first position to said second position of at least one of the sampling means causes, simultaneously, shifting from said first position to said second position of the other sampling means, thus causing said receptacle to open.

This embodiment proves particularly advantageous, insofar as it makes it possible to detect/measure several different pieces of biological and/or physicochemical information, by means of various biological and/or physicochemical information sampling means. Thus, the operator may carry out, nearly simultaneously, the detection of biological information, such as, for example, the detection of a target microorganism, and the detection of a physicochemical parameter, such as pH, for example. Obviously, the number and type of sampling means used depend on the number and nature of the biological and/or physicochemical information of interest.

According to a particular embodiment, the device according to the invention may comprise a plurality of compartments (preferably leak-proof and independent of each other, optionally included in a common container) designed to receive at least one biological sample, each compartment being advantageously connected to a common filling means (thus representing a common inlet), each of said compartments further comprising:

- at least one sampling means positioned inside the enclosure of said compartment, stationary or movable, said sampling means being designed to sample biological and/or physicochemical information from said biological sample, said sampling means being designed to be analysed after said biological and/or physicochemical information is sampled and/or placed in a release position, and
- at least one container, such as a pouch or a sub compartment, comprising at least one disinfecting agent, said disinfecting agent being designed to be released inside the compartment after said receptacle is opened,
- when said sampling means is designed to be analysed after sampling of said biological and/or physicochemical information, at least one analysis restricting means separate from said sampling means, stationary or movable, partially or completely restricting, preferably completely, the analysis of said sampling means, wherein at least a portion of said sampling means and/or at least a portion of the analysis restricting means are/is designed to shift from a first position, inside said compartment, wherein the analysis of said sampling means and/or the release of said sampling means from said compartment (or from the common container) are/is difficult or impossible, preferably impossible, to a second position, wherein the analysis of said sampling means and/or the release of said sampling means from said compartment (or from the common container) are/is possible, and wherein said portion of said sampling means and/or said portion of the analysis restricting means are/is connected to said receptacle such that the opening of said receptacle can be mechanically induced by shifting from said first position to said second position.

Advantageously, and still in this particular embodiment, the sampling means according to the present invention is designed to be contacted with the biological sample in a first position then analysed without leaving said device in a second position and/or shifted from a first position located inside said compartment ("protection position") to a release position (also called "transfer position").

Each compartment is, therefore, independent of the other compartments. Illustratively, force may be exerted on sampling means number 1 of compartment number 1, in order to carry out the analysis and/or transfer of said sampling means number 1. This mechanically (and automatically) causes the disinfection of compartment number 1 by the mechanism disclosed in the present application. On the other hand, the other compartments (compartments number 2, number 3, number 4, etc.) are not affected by the disinfection caused in compartment number 1 and the analysis and/or transfer of the biological sample in these other compartments may be carried out subsequently, the biological material not having been destroyed by the disinfecting agent released within compartment number 1.

Another object of the invention relates to a process for ensuring the disinfection of all or part of the inside of a container designed to receive at least one biological sample, said process employing the device according to the invention, said process comprising the following steps:

a) introducing via said filling means at least one biological sample into said container,
b) closing said filling means, preferably hermetically, by means of said closing means,
c) exerting force, for example of the pulling or rotational type, on at least a portion of said sampling means and/or at least a portion of said analysis restricting means in order to shift from said first position to said second position, in order to analyse and/or release said sampling means,
d) carrying out, in said second position, the analysis of said sampling means by means of at least one analysis means positioned outside said receptacle, and/or
d') releasing, in said second position (release position), said sampling means, preferably by hermetic separation, for example by heat sealing and cutting, in order to analyse all or part of said biological sample present on said sampling means during an analysis step e) performed in another container,
shifting from said first position to said second position mechanically causing said receptacle to open, thus ensuring the disinfection of all or part of said container.

The various components of the device according to the invention are as described above.

The expression "analysis means positioned outside said container" must be interpreted in the broad sense. Indeed, such an analysis means, for example in the case of a visual- or optical-type analysis, may particularly consist of the human eye or any optical reading means.

As indicated above, in step d'), the separation of said sampling means is preferably carried out by heat sealing and cutting. These two operations can be carried out via two separate operations, for example a first heat-sealing operation then a second cutting operation preferably with a sharp object, or carried out via a single operation, said operation comprising heat-sealing followed by cutting. When the environment in which the operator is located does not provide easy access to sophisticated heat-sealing devices ("heat sealers" or "heat welders") making it possible to carry out this heat-sealing in a single operation, the operator may be content to use a simple cigarette lighter to carry out the heat-sealing operation then a pair of scissors to carry out the cutting.

Analysis e) performed in another container may be performed in an independent analysis device, for example a VIDAS®-type automated analysis device.

Advantageously, in step c), pulling force is exerted on at least one gripping means connected to said portion of said sampling means and/or to said portion of said analysis restricting means.

By gripping means is meant, in the sense of the present invention, any means making it possible to take hold of or grab at least a portion of the device separate from said sampling means and/or at least a portion of said sampling means. Such a gripping means may consist of a handle, tab, pull, etc.

In other words, said portion of the device separate from said sampling means (consisting of the analysis restricting means as indicated above, for example), or the sampling means, or both, is/are equipped with such a gripping means. Preferably, pulling force is exerted on one or the other.

In order to exert this pulling force and thus to shift from said first position to said second position, the device according to the invention must be held, preferably in an area located opposite that having said gripping means. The operator may accomplish this quite simply by holding the device according to the invention in his/her hand(s). Preferably, the operator exerts said pulling force with one hand and holds the device according to the invention with the other. Advantageously, the area of the device according to the invention opposite the area comprising at least one gripping means ("first gripping means") also has at least one gripping means ("second gripping means"), such as a handle, tab, pull, etc.

According to a particular embodiment, both the first and the second gripping means are connected to the receptacle, preferably both being connected to the opening means of said receptacle. Thus, according to this particular embodiment, pulling force between the first and second gripping means causes the receptacle to open by tearing, rupturing, breaking, etc., preferably of the opening means.

According to a preferred embodiment, the biological sample is likely to contain at least one microorganism to be analysed, said process comprising, after step a), the following step:
- a') optionally contacting said biological sample with at least one cultivation means designed to allow growth of the microorganism(s) to be analysed (this cultivation means, preferably in dehydrated form, being advantageously disposed in the enclosure of the container) said process comprising, after step b) and before step c), the following step:
- b') optionally placing said device in conditions designed to allow growth of the microorganism(s) to be analysed, wherein, in step c), force, for example of the pulling or rotational type, is exerted on at least a portion of said sampling means and/or at least a portion of said analysis restricting means in order to shift from said first position, wherein the analysis of said sampling means is difficult or impossible, preferably impossible, to said second position, wherein the analysis of said sampling means is possible, in order to carry out the analysis of said sampling means without said sampling means leaving said device, preferably said process comprising step a') and optionally step b').

Step b') is necessary only if growth of the microorganism(s) to be analysed (target microorganism(s)) requires particular conditions, particularly in terms of temperature, hygrometry, light, etc.; temperature being, for example, a determining factor in terms of microorganism growth. However, if the operator employs the device and process according to the present invention in a region having a mild climate (a tropical climate, for example), it may not be necessary to use an incubator to incubate at a given temperature the biological sample comprising one or more microorganisms to be analysed and said cultivation means.

By "cultivation means designed to allow growth of the microorganism(s) to be analysed" is meant, in the sense of the present invention, a means for promoting and/or directing cultivation of the target microorganism(s) of interest. This cultivation means may, for example, be a selection agent, such as one or more antibiotics, intended to improve the selectivity of the analysis (by eliminating all or part of the undesired microorganisms (additional flora). The use of one or more antibiotics may also be justified by the fact that the target microorganism(s) is an/are antibiotic-resistant microorganism(s), namely resistant to said antibiotic(s).

The cultivation means may also be a nutrient, for example selected from vitamins, peptones, carbohydrates, etc., intended to promote the primary function of enriching in target microorganisms the biological sample tested.

Such a cultivation means may comprise or consist of a culture medium, namely a medium comprising all the elements necessary for the survival and/or growth of microorganisms and, particularly, of the microorganisms of interest (buffered peptone water, for example). The culture medium may contain optional additives, for example: peptones, one or more growth factors, carbohydrates, one or more selection agents, buffers, one or more gelling agents, one or more vitamins. This culture medium may be provided in a ready-to-use liquid or gel form, namely ready to be seeded in a tube, flask or Petri dish. The expression "culture medium" obviously includes enrichment media and broths.

According to a particularly preferred embodiment, said cultivation means is disposed beforehand in the enclosure of the container, preferably in dehydrated form. The biological sample is thus contacted with the cultivation means after introducing the biological sample into said container.

The contacting of a biological sample with at least one cultivation means as mentioned above is not necessary for biological samples likely/suspected to be naturally rich in the microorganisms to be analysed (target microorganism(s)), such as, for example, cow's milk (within the context of veterinary applications) or liquid stools (such as choleraic diarrhoeas within the context of clinical applications). When the biological sample to be analysed is sufficiently rich in microorganisms and, more precisely, likely/suspected to be naturally rich in the target microorganism(s), the use of a cultivation means proves to be superfluous and incubation time may be considerably shorter.

On the other hand, the use of cultivation means (and particularly cultivation media, such as pre-enrichment and/or enrichment broth) proves particularly important with regard to biological samples likely/suspected to contain a tiny amount of the target microorganism(s), for example on the order of a few cells in the sample. The purpose of the use of cultivation means and, particularly, culture media is to promote the growth of target microorganisms in the biological samples, if possible while limiting the growth of non-target flora.

Advantageously, said sampling means comprises at least one microorganism(s) capture means, such as a capture substrate designed to capture the microorganism(s) of interest, designed to be analysed in step d) and/or step e).

Said microorganism(s) capture means was defined above.

According to a particularly advantageous embodiment, in step d), the analysis of said sampling means is carried out by visual or optical reading (via at least one optical reading means, such as a camera or a Raman spectroscope, positioned outside said container, for example), preferably by visual reading.

Advantageously, said biological sample is contacted with a detection system designed to allow or promote said visual or optical reading, for example during step a).

Such a detection system is well-known to the skilled person and was defined above.

According to a particularly advantageous embodiment, the process according to the invention successively comprises steps d) and d'), wherein analysis step e) is an analysis confirmation step aiming to confirm or invalidate the analysis result obtained in step d).

The analysis of said sampling means is carried out, in step d), in said second position ("analysis position"), this second position corresponding or not to the release position. If this second position corresponds to the release position, once the analysis of the sampling means is carried out, said sampling means may be separated by hermetic separation (by heat sealing and cutting, for example) for purposes of subsequent analysis (additional and/or confirmation analysis).

Conversely, if in said analysis position (second position) the sampling means is not positioned in said release position, force, for example of the pulling or rotational type, is exerted on said sampling means in order to position it in its release position. Once this is carried out, it is justified to carry out step d').

Another object of the invention relates to a device designed to receive at least one biological sample and to carry out the secure transfer (namely by limiting or eliminating the risks of contamination of the environment) of at least a portion of said biological sample, said device comprising:
- at least one container, preferably leak-proof, designed to receive said biological sample, said container comprising at least one filling means, such as an opening, and at least one closing means designed to close said filling means, preferably hermetically,
- at least one movable sampling means connected to said container, said sampling means comprising at least one wall, said sampling means being designed to shift from a first position (protection position), wherein said at least one wall is protected inside said container, to a second position (release position), wherein said at least one wall projects at least partially, and preferably completely, outside said container,
- said sampling means being further designed to:
- receive, in said second position (release position), at least a portion of said biological sample in said projection of said sampling means,
- be released from said container, preferably hermetically, in said second position (release position), in order to carry out the transfer of said portion of said biological sample (to another container).

The integrity of the sampling means and, more particularly, its wall(s), is ensured in the protection position by the fact that said sampling means is positioned inside the container in said position. Thus, the device according to the invention may be stored and/or transported without the risk of damaging the sampling means. This is a significant advantage, insofar as it guarantees satisfactory operation of the device according to the invention and, even more advantageously, avoids risks of contamination of the environment (by limiting or even eliminating the risks of leaks in the wall(s) of the sampling means) during the introduction of at least a portion of the biological sample into said sampling means.

The sampling means released from the container, after release (preferably hermetic, for example by heat sealing and cutting), may be sent to a laboratory or transported thereto in a secure manner, for example for purposes of analysis. Generally, the portion of the sample contained in the released sampling means may, easily and without risks of contamination, be transferred to another container.

According to a preferred embodiment, said wall consists of a flexible membrane designed to be invaginated inside the container in said first position (protection position) and at least partially evaginated outside the container in said second position (release position).

In the sense of the present invention, this flexible membrane consists of a flexible and hermetic membrane/wall in order to avoid the risks of microbial contamination.

The first position (protection position) is a position wherein said flexible membrane is invaginated inside the container, namely penetrating by turning inside-out into a glove finger inside said container (shape of an inside-out finger of a glove).

Shifting from the protection position to the release position is carried out by turning said flexible membrane inside-out like a finger of a glove, which, in the evaginated position (release position), projects from the surface of said container in the shape of a finger of a glove.

As indicated above, this glove finger shape invaginated inside the container protects the integrity of said flexible membrane in said first position, which represents the position wherein the device according to the invention is stored and/or transported. This glove finger shape invaginated from the sampling means thus limits the risks of tearing, rupturing or other breaches in the flexible membrane constituting the sampling means during storage and transport of the device according to the invention.

Shifting said sampling means from the protection position to the release position may be carried out, for example, by applying pulling force on a gripping means connected to the outside surface of said flexible membrane or, preferably, by generating excess air pressure (by compression of at least one flexible wall of said container, for example) inside said container, in order to cause the "evagination" of said sampling means, namely the turning inside-out into a glove finger of said flexible membrane. Obviously, and particularly in the embodiment according to which said at least one flexible wall is designed to be compressed in order to cause the evagination of the sampling means by means of excess air pressure, the wall(s) and flexible membranes and, more generally, the various components of the device according to the invention are carefully selected such that their integrity is preserved during the shifting from the invaginated position to the evaginated position. This is important in order to guarantee the health and safety of the operator and his/her environment.

In this release position, the sampling means is designed to be released from said container, preferably hermetically (by heat sealing and cutting, for example), in order to carry out the transfer of all or part (preferably an aliquot) of the biological sample after the latter has been introduced into the sampling means.

The aliquot of the biological sample of interest may be introduced into the glove finger formed by the evaginated sampling means by any means, for example simply by sufficiently tilting the device according to the invention such that a portion of the biological sample flows into the evaginated sample means. An alternative for introducing the desired aliquot into the sampling means in said release position consists, for example, in compressing the container with sufficiently great intensity that a portion of the biological sample (and, optionally, of the culture medium) is transferred from said container to the sampling means in the release position (shaped like the finger of a glove, as indicated above). In the latter case, it is necessary that at least one wall of said container is deformable (made at least partially of supple or flexible material, for example), such that the compression applied to this/these deformable wall(s) can deform the latter and thus cause the transfer of at least a portion of the biological sample (and, optionally, of the culture medium) via an increase in the level in the latter within said container without danger to the operator and the environment.

Advantageously, said flexible membrane comprises at least one biological and/or physicochemical information capture means, said biological and/or physicochemical information capture means being positioned on the surface of said flexible membrane in a position designed to be in contact with the biological sample in said first position (protection position) and such that it is no longer in contact with said biological sample in said second position (release position).

The positioning of said biological and/or physicochemical information capture means on the surface of said flexible membrane is defined such that this capture means is in contact with the biological sample when said sampling means is invaginated in the container (in the protection position), namely has the shape of an inside-out finger of a glove, and such that it is no longer in contact with said biological sample in the at least partially evaginated position outside the container (in the release position), namely in the shape of a finger of a glove. Continuing the glove finger/inside-out glove finger analogy, the biological and/or physicochemical information capture means is preferably positioned at the end of the inside-out glove finger in contact with the biological sample in the first position (invaginated). This embodiment is particularly preferred since it provides the option, in addition to the fact of optionally being able to take an aliquot of the biological sample of interest for purposes of transfer as described above, of carrying out the capture of at least one piece of biological and/or physicochemical information of interest in the first position (invaginated position) by leaving said capture means in contact with the biological sample of interest for an amount of time sufficient to carry out the capture of the biological and/or physicochemical information of interest, then, secondly (when the operator estimates that the capture means has remained in contact with the biological sample for a sufficient amount of time), of carrying out the transfer of said capture means by exerting force, for example of the pulling or rotational type, on said sampling means in order to shift it from its first position (invaginated) to its release position (evaginated). Once the release position is reached, the operator may, if desired, hermetically separate (release) the sampling means containing said biological and/or physicochemical information capture means (and, optionally, an aliquot of the biological sample) in order to send said sampling means separated from the container to a laboratory for purposes of, for example, carrying out the analysis and/or analysis confirmation of said capture means "trapped" inside the heat-sealed sampling means. As indicated above, and if it is in accordance with the operator's wishes, in addition to the biological and/or physicochemical information capture means, the sampling means hermetically separated from said container may comprise an aliquot of the biological sample initially introduced into the container. This may prove advantageous particularly if it is sought to (re-)cultivate all or part of the biological material, particularly the biological material found in this aliquot.

According to a particular embodiment, before hermetic separation of the sampling means, the latter may be analysed in said release position. In this configuration, the biological and/or physicochemical information capture means is, preferably, a microorganism(s) capture means as defined above, advantageously designed to be analysed by visual or optical reading. In said release position, the flexible membrane constituting the sampling means is, in this embodiment, translucent or transparent, preferably transparent, in order to allow visual or optical reading of the microorganism(s) capture means.

Thus, the device according to the present invention provides the operator with a very wide range of use. Indeed, the operator may, if desired:
  use said device simply to transfer an aliquot of the biological sample of interest to another container in order to, for example, carry out more thorough analyses;
  transfer at least one biological and/or physicochemical information capture means having been contacted beforehand with the biological sample to be analysed to another container in order to carry out an additional analysis and/or analysis confirmation;
  carry out the analysis, preferably by visual or optical reading, of said biological and/or physicochemical information capture means present on said sampling means, in the release position, optionally prior to such a transfer, etc.

The preferential shape of the sampling means according to the invention in its first position (invaginated position), namely the shape of an inside-out glove finger whose end at least is in contact with the biological sample of interest in said first position, is particularly advantageous when at least one biological and/or physicochemical information capture means is positioned at this end in order to be in contact with the biological sample in the starting position since the operator may slip his/her finger inside the sampling means shaped like an inside-out finger of a glove in order to shift the biological and/or physicochemical information capture means to one or more areas of interest. This may have an advantage particularly if the biological sample is in semi-solid form (such as a stool sample) or if the sample is not correctly/sufficiently homogenised. Thus, the operator may manually direct the biological and/or physicochemical information capture means to/in the areas of the biological sample or may legitimately wait until the biological and/or physicochemical information of interest is present in a greater amount.

The biological and/or physicochemical information capture means is as defined above. Preferably, said biological and/or physicochemical information capture means comprises a microorganism(s) capture means, such as a capture substrate designed to capture the microorganism(s) of interest, also defined above.

According to a particular embodiment, said capture means is designed to be analysed, preferably in said release position, by visual or optical reading, preferably by optical reading via at least one optical reading means, such as a camera or a Raman spectroscope, positioned outside the container.

The invention also relates to a process for carrying out the secure transfer of at least a portion of a biological sample, said process employing the device according to the invention, said process comprising the following steps:
  a) introducing via said filling means at least one biological sample into said container,
  b) closing said filling means, preferably hermetically, by means of said closing means,
  c) exerting force, for example of the pulling or compression type, on said sampling means in order to shift from said first position (protection position) to said second position (release position), d) receiving, in said second position (release position), at least a portion of said biological sample in said projection of said sampling means, e) releasing, in said second position (release position), said sampling means, preferably by hermetic separation, for example by heat sealing and cutting, in order to carry out the transfer of said portion of said biological sample.

Preferably, said process comprises between steps d) and e), or after step e), the following step:

d') analysing said portion of said biological sample, preferably by visual or optical reading, advantageously by optical reading.

According to a particular embodiment, in step c), pulling force is exerted on at least one gripping means connected to said sampling means.

According to another particular embodiment, in step c), compressive force is exerted on said sampling means, for example by creating excess air pressure inside said container.

According to a preferred embodiment, this process comprises, during step a) or subsequent to step a), the following step:

a') contacting said biological sample with at least one cultivation means designed to allow growth of one or more target microorganisms, said process comprising, after step b) and before step c), the following step:

b') optionally placing said device in conditions designed to allow growth of the target microorganism(s).

According to a particular embodiment, said sampling means comprises at least one microorganism(s) capture means, such as a capture substrate designed to capture the microorganism(s) of interest.

The cultivation means is as defined above.

BRIEF DESCRIPTION OF THE DRAWINGS

The invention, its functionality, its applications and its advantages will be better understood upon reading the present description, made in reference to the figures, wherein.

DETAILED DESCRIPTION OF THE INVENTION

The purpose of the detailed description below is to disclose the invention in a sufficiently clear and complete manner, particularly by means of references to the figures, but should in no case be considered to limit the scope of the protection of the particular embodiments referred to by said figures.

Figure 1:
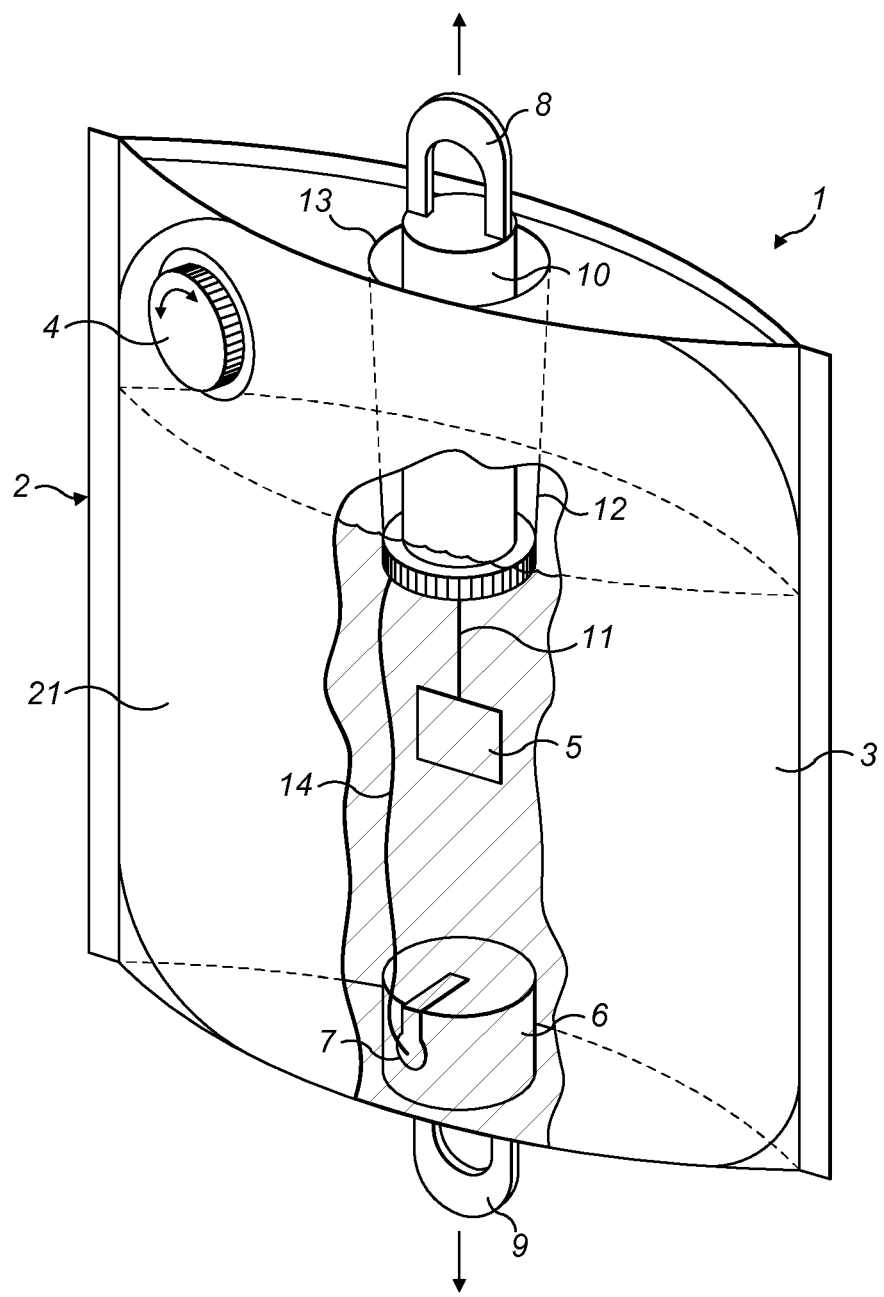
FIG. 1 shows a perspective view, and a partial cross-sectional view, of a first embodiment of the device according to the present invention.

FIG. 1 shows a first embodiment of the device 1 according to the present invention. The device 1 comprises a container 2 in bag form designed to incubate a biological sample. The container 2 comprises, for example, rigid paper, paperboard, polyethylene, polyvinyl chloride, polypropylene, polystyrene, polyethylene terephthalate, and any suitable combination of these materials and/or any other material (preferably bio-based materials) such that the container 2 has sufficient physical characteristics, particularly in terms of behaviour and sufficient sealing of the container 2. In order to carry out the incubation of said sample, a culture medium 3, such as enrichment broth, is introduced into the container 2. The container 2 is equipped with an opening able to shift from an "open" position to a "closed" position by means of a cap 4. When the cap 4 is removed, the opening may allow the introduction into the container 2 of a biological sample. After the introduction of said biological sample, the cap 4 may be used to seal the opening, preferably completely hermetically. When the biological sample has been introduced into the container 2, the culture medium 3, such as enrichment broth, is used to incubate said biological sample inside the container 2.

The device 1 is equipped with a sampling means 5. According to the embodiment shown in FIG. 1, the sampling means 5 comprises a capture substrate functionalised with a specific binding partner of the microorganism to be detected (target microorganism), such as a bacterium. The sampling means 5 is designed for a visual or optical reading-type analysis of the result of the microbiological analysis carried out by means of the device 1 according to the invention.

The device 1 is equipped with a compartment 6 comprising therein a certain amount of disinfecting agent, present preferably in concentrated form. The compartment 6 is equipped with a rupture means 7 designed to allow the opening of said compartment 6 and to thus allow the spreading inside the container 2 of the contents of this compartment 6. The compartment 6 and the rupture means 7 are designed to allow the device 1 as shown in FIG. 1 to carry out a step of disinfection of the contents of said device 1 nearly simultaneous to or simultaneous to visual or optical reading of the sampling means 5. In other words, that means that when the operator of the device 1 operates said device in a position allowing visual or optical reading of the sampling means 5, the disinfection process is carried out nearly simultaneously or simultaneously.

The operation of the device 1 as shown in FIG. 1 is ensured by virtue of the fact that the walls 21 of the container 2 are opaque. Indeed, in the first position as shown in FIG. 1, visual or optical reading of the sampling means 5 is difficult or impossible, preferably impossible. In order to make the reading of the sampling means 5 easier, or to make it possible (preferably to make it possible), the operator desiring to carry out this visual or optical reading must necessarily handle the sampling means 5 in order to shift it to a second position, wherein visual or optical reading of said sampling means 5 can be carried out. These opaque walls 21 thus constitute an analysis restricting means in the sense of the present invention.

The operation of the sampling means 5 as shown in FIG. 1 is possible by means of a first and a second handle 8, 9 present on the device 1. The first handle 8 is connected to the sampling means 5 via a tab 10 and a shank 11. The lower portion of the tab 10 is connected to the contour 13 of an opening in the upper wall of the container 2 via a flexible wall/membrane 12. It should be noted that the contour 13 may also comprise a reinforced component, such as a ring (see FIG. 5 below).

The second handle 9 is connected to the outside of the container 2 and to the lower walls of said container 2. When an operator pulls on the handles 8 and 9, in the direction indicated by arrows in FIG. 1, the sampling means 5 is shifted in the direction of the contour 13 and released from the inside of the container 2 to the outside of the container 2.

As shown in FIG. 1, the lower portion of the tab 10 is connected by means of a wire 14 to the rupture component 7 of the compartment 6 (container). Thus, the sampling means 5 is shifted in the direction of the contour 13 via the tab 10, said connection of the tab 10 to the wire 14 simultaneously causing the opening of the compartment 6 by shifting the rupture component 7 of said compartment 6. That means that as soon as the operator shifts the sampling means 5 to make visual or optical reading possible, the nearly simultaneous or simultaneous disinfection of all or part (preferably all) of the inside of the container 2 is ensured by the release and spreading of the disinfecting agent present inside the compartment 6.

Figure 2:
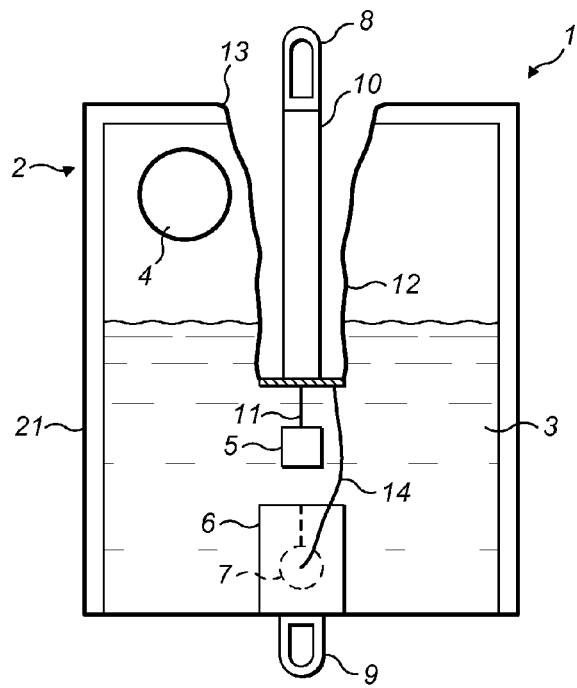
FIG. 2 shows the device as shown in FIG. 1, in cross-section, in a first position.
Figure 3:
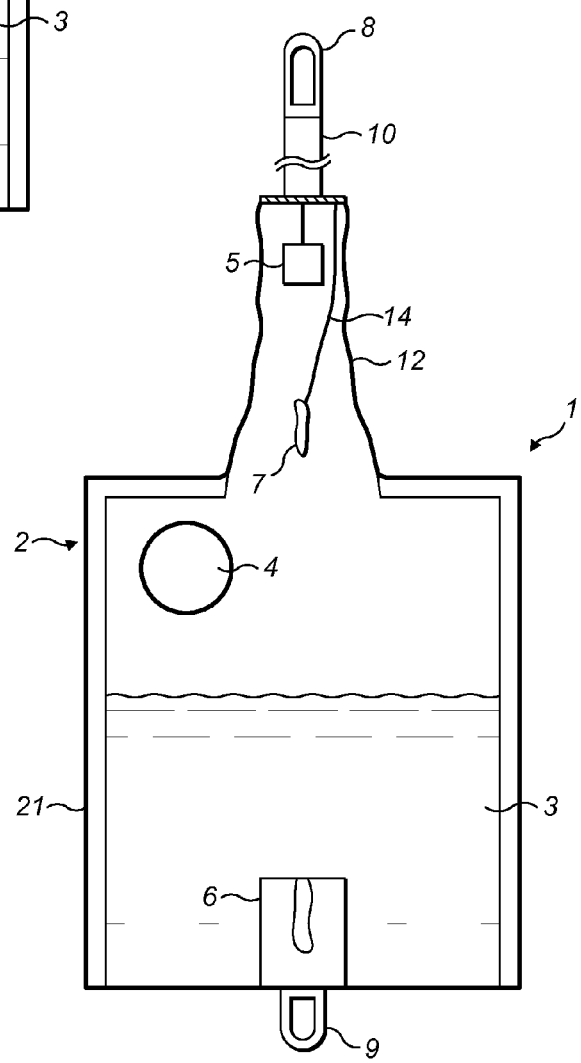
FIG. 3 shows the device as shown in FIG. 1, in cross-section, in a second position.

FIGS. 2 and 3 show the operation of the device 1 as shown in FIG. 1 and both positions of said device 1 (namely the first and second positions, respectively).

FIG. 2 shows the device 1 according to the invention in cross-section. The device 1 as shown in FIG. 2 is shown in its first configuration, identical to the configuration shown in FIG. 1.

FIG. 2 clearly shows that the sampling means 5 is, in the first configuration of the device 1, in contact with the culture medium 3, such as enrichment broth. That means that from the moment the biological sample is introduced into the container 2, the sampling means 5 allows the capture of a target bacterium, if present. The target bacterium captured on the functionalised capture substrate may be analysed in the second position by visual or optical reading.

FIG. 2 also clearly shows the presence of a flexible wall/membrane 12 between the lower portion of the tab 10 and the contour 13 of an opening in the upper wall of the container 2. Furthermore, FIG. 2 shows the connection by means of a wire 14 between the lower portion of the tab 10 and the rupture means 7 present in the compartment 6 provided.

The device 1 may be operated and shifted from its first position (shown in FIG. 2), wherein said flexible wall/membrane 12 has the shape of an inside-out glove finger inside the container 2 (invaginated position), to its second position (shown in FIG. 3), wherein said flexible wall/membrane 12 has the shape of a glove finger projecting from the surface of the container 2 (evaginated position).

In FIG. 3, it is observed that the sampling means 5 has been shifted from the inside of the container 2 to the outside thereof. The sampling means 5 remains enveloped by a flexible wall/membrane 12 in the "evaginated" position. According to the invention, the wall/membrane 12 is made of transparent material. That means that, in the second position shown in FIG. 3, visual or optical reading of the sampling means 5 is possible.

As shown in FIG. 3, after shifting from the first position (see FIG. 2) to the second position (see FIG. 3), the lower portion of the tab 10 is still connected to the rupture component 7 by means of the wire 14. By shifting the tab 10 the rupture component 7 was shifted, said shifting causing the compartment 6 inside the container 2 to open. The opening of the compartment 6 allows the release and spreading of its contents, that is, the disinfecting agent present inside the compartment 6, in the culture medium 3, such as enrichment broth, present inside the container 2.

The connection of the lower portion of the tab 10 to the rupture component 7 ensures that the content of the container 2 is disinfected simultaneously or nearly simultaneously as soon as the sampling means 5 is available for visual or optical reading. The reading of the sampling means 5 thus forces the operator to disinfect the content of the device 1 without the operator having to think about it. No specific action is needed from the operator in terms of disinfection of the container 2. After the device 1 according to the invention is used, its content is disinfected and no longer presents any biological danger with regard to storage and/or transport before its final destruction.

Figure 6:
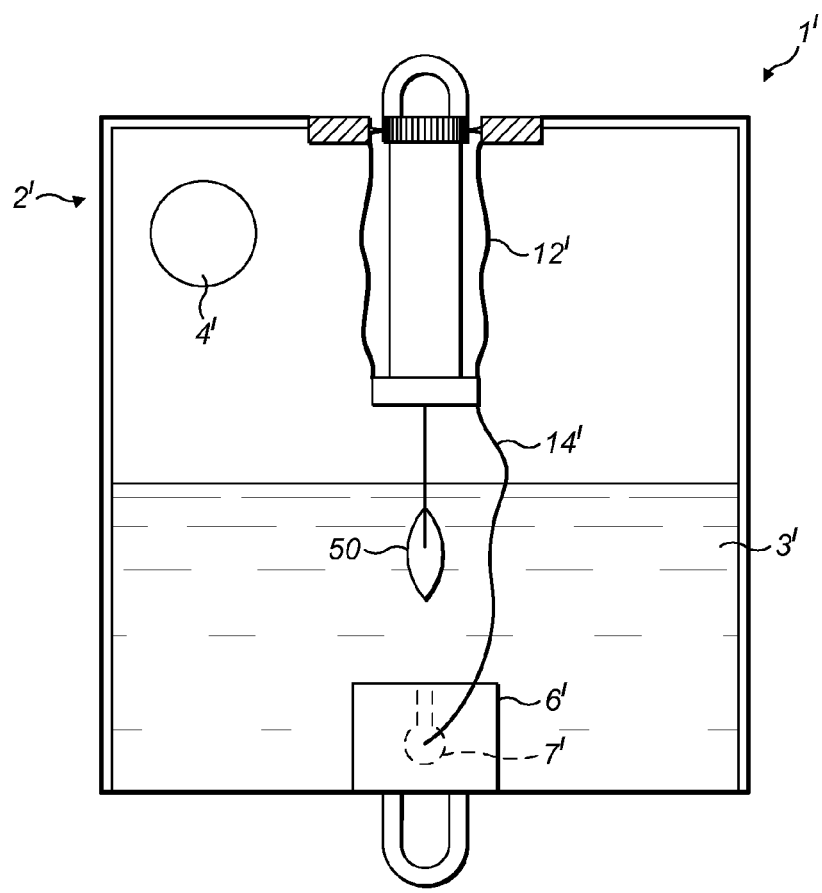
FIG. 6 is a cross-section showing a second embodiment of the device according to the invention.
Figure 7:
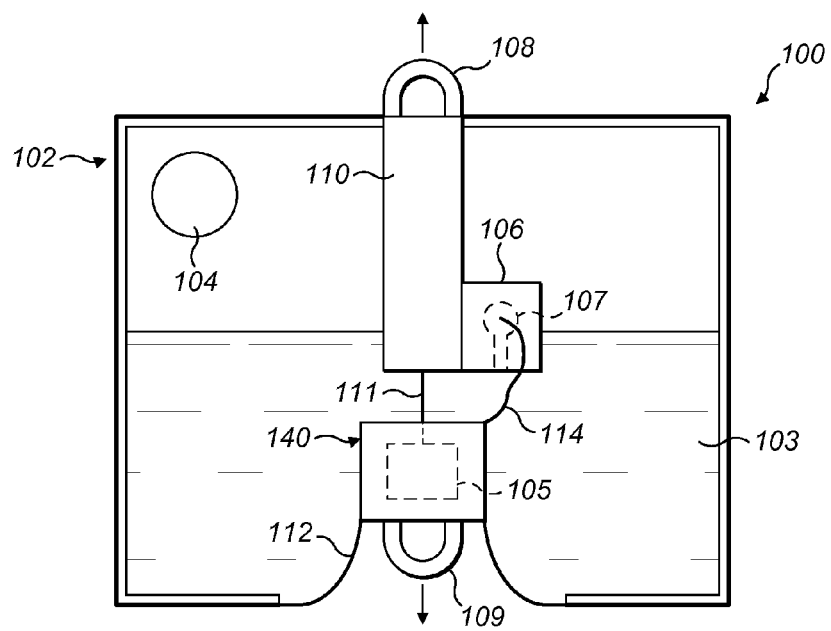
FIG. 7 shows a third embodiment of the device according to the invention, in a first position.
Figure 8:
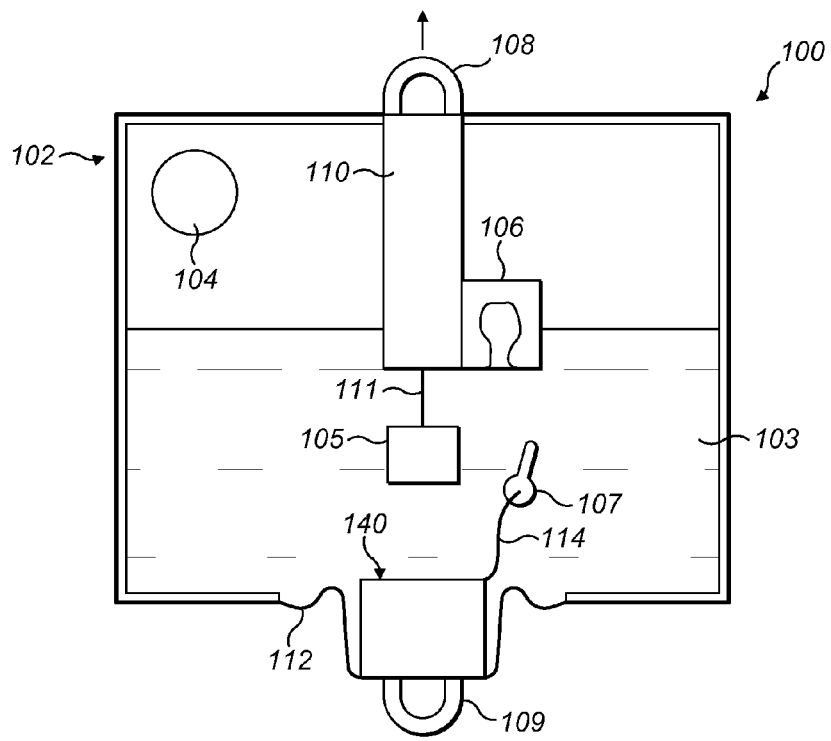
FIG. 8 shows the device as shown in FIG. 7, in a second position.
Figure 9:
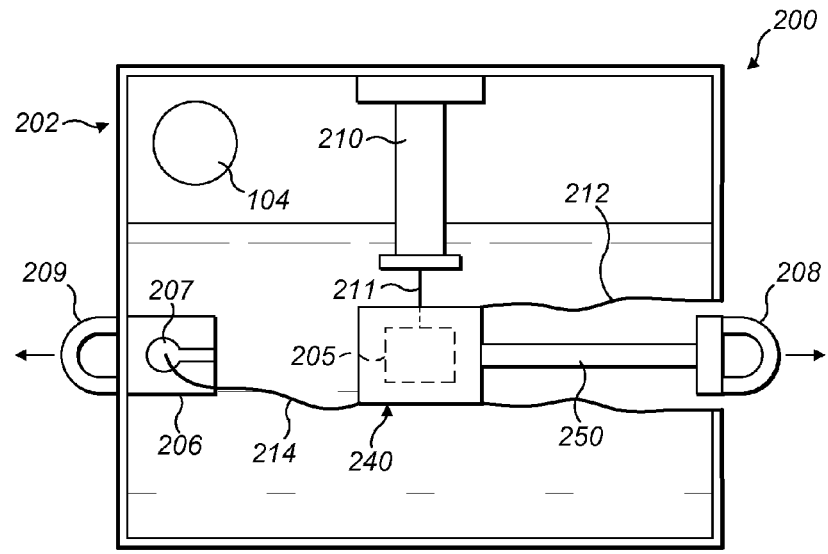
FIG. 9 shows a fourth embodiment of the device according to the invention, in a first position.
Figure 10:
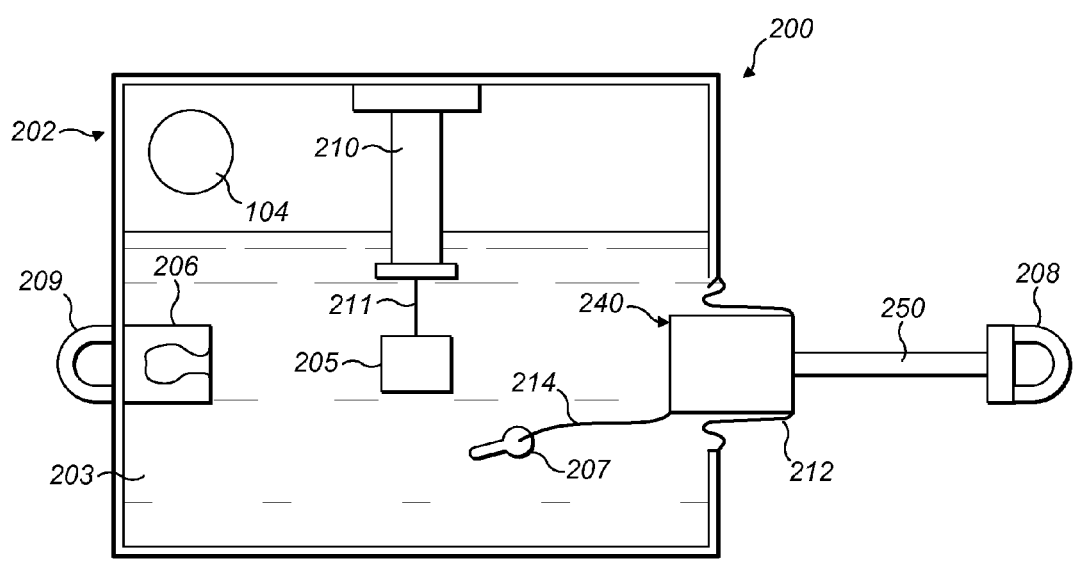
FIG. 10 shows the device as shown in FIG. 9, in a second position.
Figure 11:
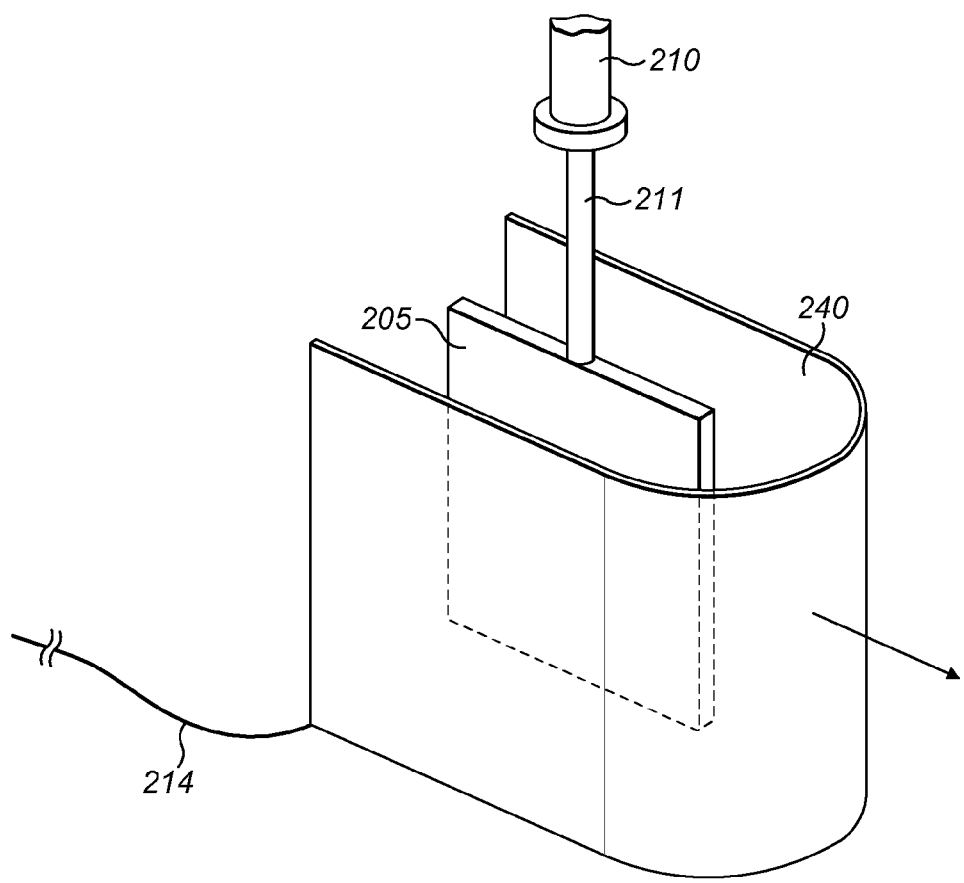
FIG. 11 is a perspective view showing the sampling means and the mask of the device as shown in FIG. 9.

It should be noted that the sampling means 5 may comprise any sampling means designed to measure one or more biological and/or physicochemical parameters of a sample. That means that the sampling means 5 may comprise, in addition to a functionalised capture substrate designed to capture a target bacterium, a component designed to transfer a certain amount of a biological sample for purposes of subsequent analysis. Such a component may comprise, for example, a spongy component (such as cotton) or compressible component (such as sponge), positioned at the end of a shank, designed to absorb a certain amount of biological sample. A component of this type is shown in FIG. 6.

According to a preferred embodiment of the invention, the sampling means 5 may be released/separated from the container 2 of the device according to the invention by preserving the hermetic side of the sheath of said sampling means and by ensuring that the container 2 remains hermetically closed.

Figure 4:
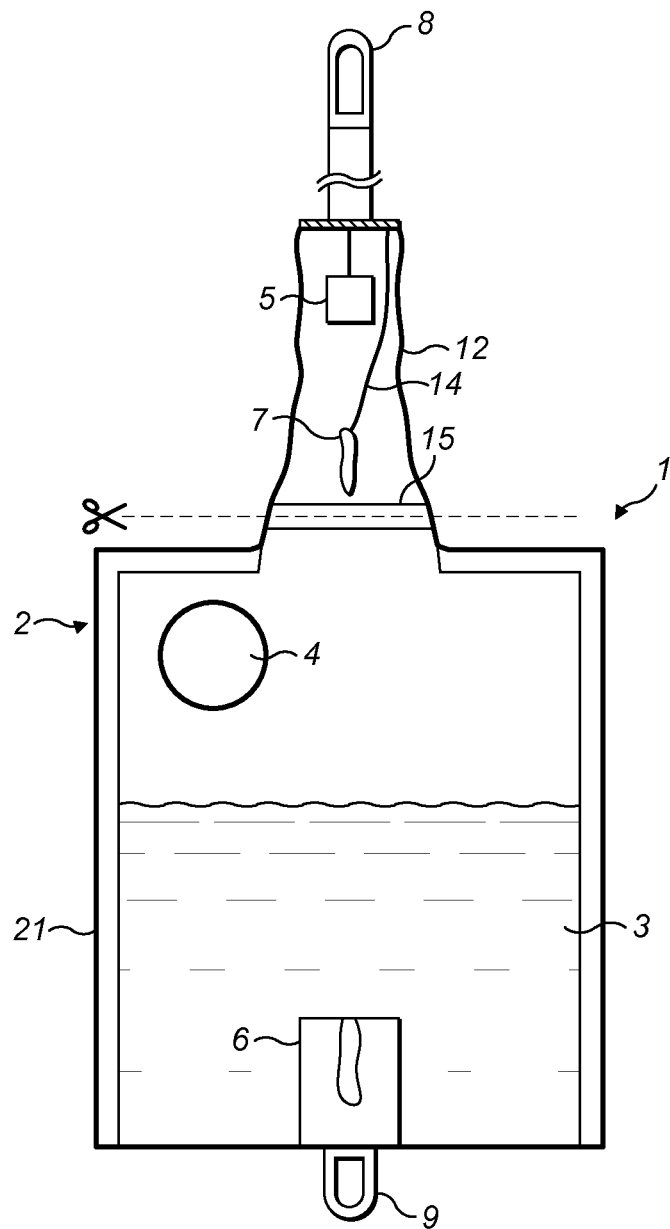
FIG. 4 shows the device as shown in FIG. 3, after a heat-welding (heat-sealing) process for preparing the release of the biological and/or physicochemical information sampling means.
Figure 4A:
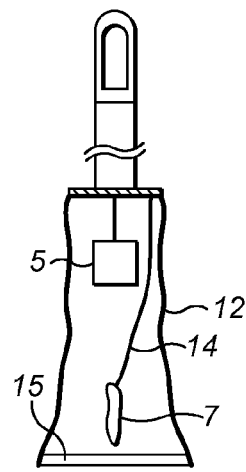
FIGS. 4a and 4b show the device as shown in FIG. 4, after the release of said sampling means.
Figure 4B:
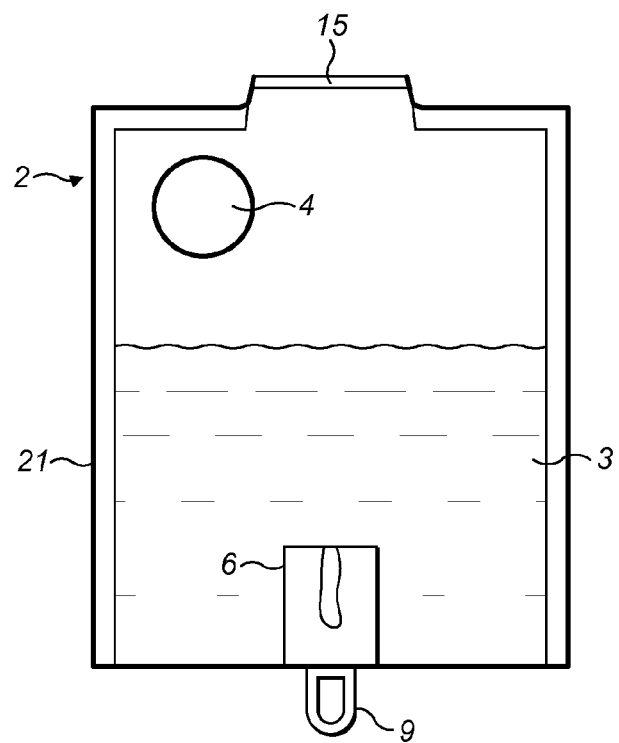

FIGS. 4, 4a and 4b show an option of separating in a hermetic (leak-proof) manner a portion of the device 1 comprising the sampling means 5.

FIG. 4 shows the device 1 according to the invention in its second position. The sampling means 5 is enveloped by the flexible wall/membrane 12. In order to prepare the separation of the sampling means 5 from the container 2, optionally after the sampling means 5 has been analysed by visual or optical reading in said second position, a first step consists in a process of heat welding (heat sealing) to create a welded area 15. The purpose of this welded area 15 is, first, to hermetically close (namely by sealing) the upper wall of the container 2. Simultaneously, the flexible wall/membrane 12 is hermetically closed in its lower portion. When the welded area 15 is created, it can be used to separate the portion comprising the sampling means 5 from the container 2. This separation is shown in FIGS. 4a and 4b. First, the container 2, comprising in its interior an amount of disinfected biological material, is hermetically sealed. The welded area 15 guarantees hermetic closure of the portion comprising the sampling means 5, the latter itself being hermetically closed. To allow this process, the material used to make the wall 12 must be selected for its ability to be used in a heat-welding process.

If need be, an operator may proceed with the introduction into the portion comprising the sampling means 5 of a certain amount of biological material, in practice a certain amount of medium composed of the biological sample and culture medium. The presence of the welded area 15 guarantees the leak-resistance of any biological material enveloped by the wall 12 and the welded area 15 during storage and/or transport.

Figure 5:
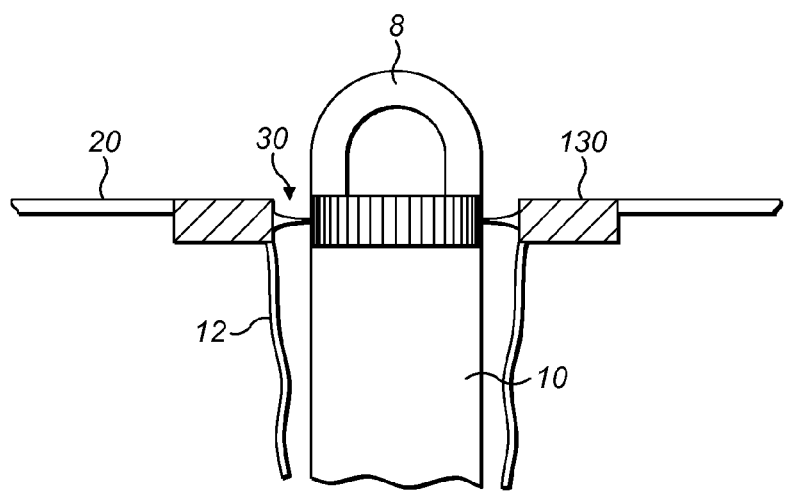
FIG. 5 shows a detailed view of the device as shown in FIGS. 1-4, comprising a tamper-evident means.

FIG. 5 shows a portion of the device 1 according to the invention in an embodiment comprising tamper-evident means. According to the embodiment shown in FIG. 5, the contour 13 comprises a ring 130. This ring 130 is made, for example, of material allowing attachment, on said ring 130, of a portion of the upper wall 20 of the container 2 and the flexible wall/membrane 12. The tamper-evident means 30 are present between the ring 130 and the upper portion of the tab 10. These tamper-evident means 30 consist, for example, of bridges of plastic material connecting the ring 130 to the upper parts of the tab 10. A primary objective of these tamper-evident means 30 consists in making it possible to correctly position the tab 10 inside the container 2 before its use. When the operator wishes to use the device 1 according to the invention, the tamper-evident means are destroyed during first use, that is, their presence in no way obstructs the normal use of the device 1 according to the invention. On the other hand, when the tamper-evident means are destroyed, visible proof of the use of the device 1 according to the invention is provided. Any operator is thus able to determine with the naked eye whether a device 1 is new or used.

FIG. 6 shows a second embodiment of the device 1 according to the invention. The device 1' as shown in FIG. 6 comprises a shank-shaped sampling means 50 comprising a spongy means, such as cotton, said spongy means having the ability to absorb at least a certain amount of biological material diluted in culture medium 3', such as enrichment broth, present inside the container 2'.

Unlike the sampling means 5 shown in FIG. 1, the sampling means 50 is not designed to specifically capture and detect target microorganisms by visual or optical analysis, for example. On the other hand, this sampling means 50 is designed to absorb a certain amount of biological material and to transfer it inside the wall 12' when the device 1' is shifted from its first position, as shown in FIG. 6, to its second position (release/transfer position, not shown), in a manner similar to the operation shown in FIGS. 2 and 3 and described with reference to said figures.

As described in reference to FIGS. 4, 4*a* and 4*b*, the sheath formed by the flexible wall/membrane 12 and the welded area 15 may be used to hermetically envelop the sampling means 50 for transport or for carrying out subsequent analysis.

FIG. 7 shows a third embodiment of the device 100 according to the invention. The device 100 comprises a container 102 designed to receive therein culture medium 103, such as enrichment broth. Moreover, a sampling means 105 is present inside the container 102. The device 100 comprises an opening hermetically sealed by means of a cap 104. When the cap 104 is removed, a biological sample may be introduced into the container 102. The sampling means 105 is designed to detect and capture a target bacterium inside the container 102. The sampling means 105 is also designed for visual or optical analysis. The device 100 as shown in FIG. 7 comprises a container 102 equipped with partially transparent walls. That means that the visual or optical analysis of the sampling means 105 is possible through the walls of the container 102.

In order to force on an operator a specific use of the device 100 as shown in FIG. 7, the device 100 comprises a mask 140 (representing an analysis restricting means in the sense of the present invention), said mask 140 being designed to form an opaque wall that renders difficult or impossible (preferably impossible) visual or optical reading of the sampling means 105. The mask 140 present inside the device 100 may be shifted. It may be shifted from a first position, as shown in FIG. 7, to a second position, as shown in FIG. 8. In order to disinfect the content of the container 102 simultaneous to or nearly simultaneous to the optical or visual reading of the sampling means 105, the mask 140 is attached by means of a wire 114 to a rupture component 107 present on a receptacle 106. The receptacle 106 is designed to receive therein an amount of disinfecting agent, preferably in concentrated form. Shifting of the mask 140 from its position as shown in FIG. 7 ("first position") to its position as shown in FIG. 8 ("second position") renders visible the sampling means 105, thus allowing visual or optical reading of said sampling means 105. The connection between the mask 140 and the rupture component 107, by means of the wire 114, causes the receptacle 106 to open and to release its contents inside the container 102, since the mask 140 is shifted from its first position to its second position. The opening of the receptacle 106 and the release of its contents are shown in FIG. 8.

FIG. 9 shows a fourth embodiment of the device according to the invention, according to which a device 200 according to the invention comprises a container 202 designed to receive therein a culture medium 203, such as enrichment broth. A sampling means 205 is present inside the container 202. This sampling means 205 is held in place by means of a tab 210 and a shank 211. The container 202 comprises walls that are at least partially transparent and thus make visible the sampling means 205 through the walls of the container 202. On the other hand, in order to force on an operator an automatic disinfection step, the device 200 comprises a movable mask 240 that can be shifted by means of a handle 208 connected to the mask by means of a shank 250. The mask 240 may be shifted from its position, as shown in FIG. 9 ("first position"), to its position as shown in FIG. 10 ("second position") by pulling on the two handles 208 and 209 in the direction indicated by the arrows shown in FIG. 9.

The mask 240 is designed to make it difficult or impossible (preferably impossible) to read the sampling means 205 in the position shown in FIG. 9 ("first position"). It is possible to read the sampling means 205 in the position shown in FIG. 10 ("second position"). The mask 240 is connected by means of a wire 214 to a rupture component 207. The rupture component 207 itself is connected to a container 206 comprising an amount of disinfecting agent(s), said disinfectant being preferably in concentrated form. Shifting the shank 240 from its position as shown in FIG. 9 to its position as shown in FIG. 10 causes the rupture component 207 to shift, thus allowing the contents of the container 206 to be spread inside the container 202. The opening of the container 206 is shown in FIG. 10.

FIG. 11 shows a particular embodiment of the mask 240 playing the role of analysis restricting means in the sense of the present invention. The mask 240 as shown in FIG. 11 has a curved shape that covers two sides of the sampling means 205.

The device and the process according to the present invention also make it possible to perform sterility verifications, particularly in food and environmental samples. To this end, a device according to the present invention comprising at least one sampling means is used, said sampling means comprising generic means for detecting microorganisms, such as capture substrates functionalised with generic binding partners of the anti-Gram-negative, anti-Gram-positive type, etc.

The invention claimed is:
1. A device designed to receive at least one biological sample, the device comprising:
at least one leak-proof container designed to receive at least one biological sample, the at least one leak-proof container comprising an enclosure, at least one filling means, and at least one closing means designed to hermetically close the at least one filling means;
at least one sampling means positioned inside the enclosure of the at least one leak-proof container, the at least one sampling means designed to sample biological and/or physicochemical information from the at least one biological sample, the at least one sampling means further designed to be analysed after the biological and/or physicochemical information is sampled and/or placed in a release position;
at least one receptacle comprising at least one disinfecting agent designed to be released inside the at least one leak-proof container after the at least one receptacle is opened; and
when the at least one sampling means is designed to be analysed after the biological and/or physicochemical information is sampled, at least one analysis restricting means designed to restrict the analysis of the at least one sampling means;
wherein at least one of at least a portion of the at least one sampling means and/or at least a portion of the at least one analysis restricting means is/are designed to shift from a first position to a second position, wherein the first position is designed to prevent the analysis of the at least one sampling means and/or the release of the at least one sampling means from the at least one leak-proof container, wherein the second position is designed to provide for analysis of the at least one sampling means and/or release of the sampling means from the at least one leak-proof container; and
wherein at least one of the portion of the at least one sampling means and the portion of the at least one analysis restricting means is connected to the at least one receptacle such that an opening of the at least one receptacle is mechanically induced by shifting from the first position to the second position.
2. The device of claim 1, wherein the at least one sampling means is designed to be analysed in the second position, the at least one sampling means comprising at least one biological and/or physicochemical information capture means designed to be contacted with the at least one biological sample in the first position and analysed in the second position.
3. The device of claim 2, wherein the capture means is designed to be analysed, in the second position, by visual or optical reading of the at least one analysis restricting means, and wherein a light restricting component at least partially restricts transmission of light information between the at least one sampling means and a human eye or an optical reading means in the first position.
4. The device of claim 3, wherein the light restricting component comprises at least one of at least one opaque area on at least one wall of the at least one leak-proof container and/or a movable mask positioned inside the at least one leak-proof container.

5. The device of claim 2, wherein the at least one biological and/or physicochemical information capture means comprises a microorganism capture means designed to capture at least one microorganism of interest, the microorganism capture means being designed to be analysed, after capture of the at least one microorganism of interest, by at least one analysis means.
6. The device of claim 1, wherein when the at least one sampling means is designed to be placed in a release position, the at least one sampling means comprising a flexible membrane connected to the at least one leak-proof container, the flexible membrane being designed to be invaginated inside the at least one leak-proof container in the first position and at least partially evaginated outside the at least one leak-proof container in the second position.
7. The device of claim 6, wherein the flexible membrane comprises at least one biological and/or physicochemical information capture means, the at least one biological and/or physicochemical information capture means being positioned on a surface of the flexible membrane in contact with the at least one biological sample in the first position and not in contact with the at least one biological sample in the second position.
8. The device of claim 1, wherein the at least one receptacle further comprises at least one marker for verifying release of the at least one disinfecting agent inside the at least one leak-proof container after the at least one receptacle is opened.
9. The device of claim 1, wherein the at least one sampling means is connected to the at least one leak-proof container by a tamper-evident means.
10. The device of claim 1, further comprising a plurality of sampling means positioned inside the enclosure of the at least one leak-proof container, the plurality of sampling means being joined together such that a shifting from the first position to the second position of at least one of the plurality of sampling means simultaneously causes the plurality of sampling means to shift from the first position to the second position, thus causing the at least one receptacle to open.
11. A process for disinfecting an inside of an at least one leak-proof container designed to receive at least one biological sample, the process employing a device comprising at least one leak-proof container designed to receive at least one biological sample, the at least one leak-proof container comprising an enclosure, at least one filling means, and at least one closing means designed to hermetically close the at least one filling means; at least one sampling means positioned inside the enclosure of the at least one leak-proof container, the at least one sampling means designed to sample biological and/or physicochemical information from the at least one biological sample, the at least one sampling means further designed to be analysed after the biological and/or physicochemical information is sampled and/or placed in a release position; at least one receptacle comprising at least one disinfecting agent designed to be released inside the at least one leak-proof container after the at least one receptacle is opened; and when the at least one sampling means is designed to be analysed after the biological and/or physicochemical information is sampled, at least one analysis restricting means designed to restrict the analysis of the at least one sampling means; wherein at least one of at least a portion of the at least one sampling means and/or at least a portion of the at least one analysis restricting means are/is designed to shift from a first position to a second position, wherein the first position is designed to prevent the analysis of the at least one sampling means and/or the release of the at least one sampling means from the at least one leak-proof container, wherein the second position is designed to provide for analysis of the at least one sampling means and/or release of the at least one sampling means from the at least one leak-proof container; and wherein at least one of the portion of the at least one sampling means and the portion of the at least one analysis restricting means is connected to the at least one receptacle such that an opening of the at least one receptacle is mechanically induced by shifting from the first position to the second position, the process comprising:
 a) introducing, via the at least one filling means, at least one biological sample into the at least one leak-proof container;
 b) hermetically closing the at least one filling means by means of the at least one closing means;
 c) exerting a force on at least one of at least a portion of the at least one sampling means or at least a portion of the at least one analysis restricting means, thereby shifting at least one of at least a portion of the at least one sampling means or at least a portion of the at least one analysis restricting means from a first position to a second position in order to analyse or release the at least one sampling means; and at least one of:
 d) carrying out, in the second position, the analysis of the at least one sampling means by at least one analysis means positioned outside the at least one leak-proof container, and
 d') releasing, in the second position, the at least one sampling means in order to analyse all or part of the at least one biological sample present on the at least one sampling means during further analysis e) performed in another at least one leak-proof container,
 wherein shifting from the first position to the second position mechanically causes the at least one receptacle to open, thus resulting in disinfection of all or part of the at least one leak-proof container.

12. The process of claim 11, wherein exerting a force in c) comprises exerting a pulling force on at least one gripping means connected to a portion of the at least one sampling means or to a portion of the at least one analysis restricting means.

13. The process of claim 11, wherein exerting a force in c) comprises exerting force on at least one of at least a portion of the at least one sampling means or at least a portion of the at least one analysis restricting means in order to shift from the first position to the second position, wherein the first position is designed to prevent the analysis of the at least one sampling means, and wherein the second position is designed to provide for the analysis of the at least one sampling means without removing the at least one sampling means from the device.

14. The process of claim 11, wherein if the at least one biological sample is likely to contain at least one microorganism to be analysed, the process further comprises during or subsequent to a):
 a') contacting the at least one biological sample with at least one cultivation means designed to allow growth of the at least one microorganism to be analysed; and
 the process further comprising, after step b) and before step c)
 b') placing the device in conditions designed to allow growth of the at least one microorganism to be analysed.

15. The process of claim 14, wherein the at least one sampling means comprises at least one microorganism capture means designed to capture the at least one microorganism of interest for analysis in at least one of d) and/or e).

16. The process of claim 11, wherein the analysis of the at least one sampling means in d) is performed by visual or optical reading.

17. The process of claim 16, further comprising contacting the at least one biological sample with a detection system designed to allow or promote the visual or optical reading.

18. The process of claim 11, the process successively comprising d) and d'), further comprising confirming or invalidating a result of the analysis of the at least one sampling means obtained in d).

19. A device designed to receive at least one biological sample and to carry out a secure transfer of at least a portion of the at least one biological sample, the device comprising:
 at least one leak-proof container designed to receive the at least one biological sample, the at least one leak-proof container comprising at least one filling means and at least one closing means designed to hermetically close the at least one filling means;
 at least one movable sampling means connected to the at least one leak-proof container and comprising at least one wall, the at least one movable sampling means being designed to shift from a first position to a second position, wherein the at least one wall is protected inside the at least one leak-proof container in the first position, and wherein the at least one wall projects at least partially outside the at least one leak-proof container in the second position;
 wherein the at least one movable sampling means is further designed to:
  receive, in the second position, at least a portion of the at least one biological sample in a projection of the at least one movable sampling means, and
  be hermetically separable from the at least one leak-proof container in the second position, in order to carry out the transfer of the portion of the at least one biological sample.

20. The device of claim 19, wherein the at least one wall comprises a flexible membrane designed to be invaginated inside the at least one leak-proof container in the first position and at least partially evaginated outside the at least one leak-proof container in the second position.

21. The device of claim 20, wherein the flexible membrane comprises at least one biological and/or physicochemical information capture means, the at least one biological and/or physicochemical information capture means being positioned on a surface of the flexible membrane in contact with the at least one biological sample in the first position and not in contact with the at least one biological sample in the second position.

22. A process for carrying out a secure transfer of at least a portion of at least one biological sample, the process employing a device comprising at least one leak-proof container designed to receive the at least one biological sample, the at least one leak-proof container comprising at least one filling means and at least one closing means designed to hermetically close the at least one filling means; at least one movable sampling means connected to the at least one leak-proof container and comprising at least one wall, the at least one movable sampling means being designed to shift from a first position to a second position, wherein the at least one wall is protected inside the at least one leak-proof container in the first position, and wherein the at least one wall projects at least partially outside the at least one leak-proof container in the second position; wherein the at least one movable sampling means is further designed to: receive, in the second position, at least a portion of the at least one biological sample in a projection of the at least one movable sampling means, and be hermetically released from the at least one leak-proof container in the second position, in order to carry out the transfer of the portion of the at least one biological sample, the process comprising:

a) introducing the at least one biological sample into the at least one leak-proof container via the at least one filling means;

b) hermetically closing the at least one filling means by means of the at least one closing means;

c) exerting a force on the at least one movable sampling means in order to shift the sampling means from a first position to a second position;

d) receiving, in the second position, at least a portion of the at least one biological sample in a projection of the at least one movable sampling means; and e) separating, in the second position, the at least one movable sampling means from the at least one leak-proof container, thereby transferring the portion of the at least one biological sample.

23. The process of claim 22, further comprising, during a) or subsequent to a), the following:

a') contacting the at least one biological sample with at least one cultivation means designed to allow growth of one or more target microorganisms; and the process comprising, after b) and before c), the following b') placing the device in conditions designed to allow growth of the one or more target microorganisms.

24. The process of claim 23, wherein the at least one movable sampling means comprises at least one microorganism capture means designed to capture the one or more target microorganisms.

25. The device of claim 3, wherein the light restricting component completely restricts transmission of light information between the at least one sampling means and the human eye or the optical reading means in the first position.

26. The device of claim 8, wherein the at least one marker comprises a coloured marker.

27. The device of claim 9, wherein the tamper-evident means comprises a tamper evident ring.

* * * * *